(12) United States Patent
Nishimura et al.

(10) Patent No.: US 6,809,239 B1
(45) Date of Patent: Oct. 26, 2004

(54) CHOLINE MONOOXYGENASE GENE

(75) Inventors: Satoru Nishimura, Toyota (JP); Ayumi Koike, Yokohama (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/534,995

(22) Filed: Mar. 27, 2000

(30) Foreign Application Priority Data

Sep. 27, 1999 (JP) ............................................ 11-273275

(51) Int. Cl.$^7$ ............................. A01H 5/00; G12N 5/02; C12N 15/70; C07H 21/04
(52) U.S. Cl. ............................... 800/317.3; 435/320.1; 435/410; 536/23.6
(58) Field of Search ............................. 435/320.1, 410; 536/23.2; 800/317.3

(56) References Cited

U.S. PATENT DOCUMENTS 6,310,271 B1 * 10/2001 Hanson et al. .............. 800/278

FOREIGN PATENT DOCUMENTS

EP         WO 98/30702      *  1/1998

OTHER PUBLICATIONS

Nuccio at at, The endogenous choline supply limits glycine betaine synthesis in transgenic tobacco expressing choline monooxygenase, 1998, The Plant Journal, vol. 16, No. 4, pp. 487–496.*
Rathinasabapathi et al, Choline monooxygenase, an unusual iron–sulfur enzyme catalyzing the first step of glycine betaine synthesis in plants: Prosthetic group characterization and cDNA cloning, Apr. 1997, Plant Biology, vol. 94, pp. 3454–3458.*
Barosci et al. Optimizing Phytoremediation of Heavy Metal–Contaminated Soil by Exploiting Plants' Stress Adaptation. International Journal of Phytoremediation. Mar. 2003, vol. 5, No. 1, pp. 13–23.*
Flavell, R. B., et al., Instability of transgenes in plants and its implications for plant breeding. Techniques for Crop Improvement, Viena, Jun. 19–23, 1995, pp. 13–22.*
Palowski et al. Irregular patterns of trangene silencing in allohexaploid oat. Plant Molecular Biology, Nov., 1998, vol. 38, No. 4, pp. 597–607.*
Fromm et al. Mechansims governing plant responses to environmental stress. http://www.weizmann.ac.il/Biology/open–day/images/hillel.pdf.*
Deak et al. Plants ectopically expressing the iron–binding protein, ferritin, are tolerant to oxidative damage and pathogens. Nature Blotechnology. vol. 17, Feb. 1999, pp. 192–196.*
The Japanese Society of Plant Physiologists, 1999 Annual Conference and the 39th Symposium of the Japanese Society of Plant Physiologists, Mar. 28–30, 1999.

* cited by examiner

*Primary Examiner*—Karen A. Lacourciere
*Assistant Examiner*—Janet L. Epps-Ford
(74) *Attorney, Agent, or Firm*—Oblon, Spivak, McClelland, Maier & Neustadt, P.C.

(57) ABSTRACT

According to the present invention, plant choline monooxygenase and the gene thereof are provided. The present invention discloses the following recombinant proteins (a) and (b) as well as genes encoding the proteins:

(a) comprising the amino acid sequence shown in SEQ ID NO: 2, 4 or 6;
(b) comprises the amino acid sequence shown in SEQ ID NO: 2, 4 or 6 having deletion, substitution or additon of one or several amino acids, and which has choline monooxygenase activity.

39 Claims, 1 Drawing Sheet

SALT STRESS RESPONSIVITY OF CMO TRANSIT PEPTIDE

BETAINE ACCUMULATION IN TRANSGENIC TOBACCO

SEQUENCE LISTING

```
<160> NUMBER OF SEQ ID NOS: 17

<210> SEQ ID NO 1
<211> LENGTH: 1828
<212> TYPE: DNA
<213> ORGANISM: Chenopodium album
<220> FEATURE:
<221> NAME/KEY: CDS
<222> LOCATION: (129)..(1427)
<223> OTHER INFORMATION:

<400> SEQUENCE: 1
gaactataca agctaagtta agcttaagct atattgttga tcatctttca tactacttcc      60
tttaaaaaaa aaattataac aacaaaagga agtgtgaatt ttttccttga tcatcatata     120 acatcaat atg gca gca agt gca aca aca atg ttg ctg aaa tac cca aca     170
         Met Ala Ala Ser Ala Thr Thr Met Leu Leu Lys Tyr Pro Thr
         1               5                   10 act gta tgt ggt ata cca aat tca tca tca aac aat gat act tca aat     218
Thr Val Cys Gly Ile Pro Asn Ser Ser Ser Asn Asn Asp Thr Ser Asn
15                  20                  25                  30 aat ata gtc cca att cca caa act agt act aat aat ccg gta ctt aag     266
Asn Ile Val Pro Ile Pro Gln Thr Ser Thr Asn Asn Pro Val Leu Lys
                35                  40                  45 ttt cgt acc cct aat aaa acc att aac gcc gtc gct gcc ccg gct ttt     314
Phe Arg Thr Pro Asn Lys Thr Ile Asn Ala Val Ala Ala Pro Ala Phe
            50                  55                  60 cct tct tta aac acc acc act act ccg ccg tcg att caa tca ctt gtc     362
Pro Ser Leu Asn Thr Thr Thr Thr Pro Pro Ser Ile Gln Ser Leu Val
        65                  70                  75 cag gaa ttc gat ccg aag att ccg gct aag gat gct ctt acg cct cct     410
Gln Glu Phe Asp Pro Lys Ile Pro Ala Lys Asp Ala Leu Thr Pro Pro
    80                  85                  90 agc tct tgg tat act gac gct gct ttc tat gct cat gaa ctt gac cgt     458
Ser Ser Trp Tyr Thr Asp Ala Ala Phe Tyr Ala His Glu Leu Asp Arg
95                  100                 105                 110 atc ttt tat aag gga tgg caa gtc cca ggg tac agt gat caa att aag     506
Ile Phe Tyr Lys Gly Trp Gln Val Pro Gly Tyr Ser Asp Gln Ile Lys
                115                 120                 125
```

```
gag cct aac caa tat ttc acc gga acg tta gga aat gtt gaa tat ttg     554
Glu Pro Asn Gln Tyr Phe Thr Gly Thr Leu Gly Asn Val Glu Tyr Leu
        130                 135                 140 gtg tgt cga gat ggt gaa gga aaa gtt cat gca ttt cac aac gtt tgc     602
Val Cys Arg Asp Gly Glu Gly Lys Val His Ala Phe His Asn Val Cys
145                 150                 155 acc cat cgt gct tcg att ctt gct tgt gga agt gga aaa aaa tcg tgt     650
Thr His Arg Ala Ser Ile Leu Ala Cys Gly Ser Gly Lys Lys Ser Cys
        160                 165                 170 ttt gtg tgc cct tac cat gga tgg gta ttt ggc atg aat gga tcg ctt     698
Phe Val Cys Pro Tyr His Gly Trp Val Phe Gly Met Asn Gly Ser Leu
175                 180                 185                 190 aca aaa gct tcc aaa gca acc gaa gaa cag tca ctt gat ccc gat gaa     746
Thr Lys Ala Ser Lys Ala Thr Glu Glu Gln Ser Leu Asp Pro Asp Glu
            195                 200                 205 ctt ggg ctt gta ccc ctg aaa gtt gca gta tgg ggc cca ttt ata ctc     794
Leu Gly Leu Val Pro Leu Lys Val Ala Val Trp Gly Pro Phe Ile Leu
        210                 215                 220 ata agt ttg gac aga tca agc ctt gaa gta ggt gat gtt gga tct gaa     842
Ile Ser Leu Asp Arg Ser Ser Leu Glu Val Gly Asp Val Gly Ser Glu
225                 230                 235 tgg ctt ggt agt tgt gct gaa gat gtt aag gcc cat gct ttt gac cct     890
Trp Leu Gly Ser Cys Ala Glu Asp Val Lys Ala His Ala Phe Asp Pro
        240                 245                 250 aat tta cag ttc atc aat agg agt gaa ttt cca atg gaa tct aat tgg     938
Asn Leu Gln Phe Ile Asn Arg Ser Glu Phe Pro Met Glu Ser Asn Trp
255                 260                 265                 270 aag att ttc agt gac aac tat ttg gat agc tcg tac cat gtt cct tat     986
Lys Ile Phe Ser Asp Asn Tyr Leu Asp Ser Ser Tyr His Val Pro Tyr
                275                 280                 285 gca cac aag tac tat gct act gaa ctc gac ttt gat act tac caa act    1034
Ala His Lys Tyr Tyr Ala Thr Glu Leu Asp Phe Asp Thr Tyr Gln Thr
        290                 295                 300 gat atg atc gga aac gtc acg att caa aga gtg gca ggg agt tca aac    1082
Asp Met Ile Gly Asn Val Thr Ile Gln Arg Val Ala Gly Ser Ser Asn
        305                 310                 315 aat ggt ttt aat aga ctt gga tct caa gca ttc tat gct ttt gca tac    1130
Asn Gly Phe Asn Arg Leu Gly Ser Gln Ala Phe Tyr Ala Phe Ala Tyr
        320                 325                 330 cct aac ttt gct gtg gaa agg tat ggc cct tgg atg aca aca atg cac    1178
Pro Asn Phe Ala Val Glu Arg Tyr Gly Pro Trp Met Thr Thr Met His
335                 340                 345                 350 att ctt cca tta gga cca agg aaa tgc aaa tta gtg gtg gac tac tac    1226
Ile Leu Pro Leu Gly Pro Arg Lys Cys Lys Leu Val Val Asp Tyr Tyr
            355                 360                 365 att gaa aaa tca aag ctg gac gac aag gat tac atc gag aag ggc att    1274
Ile Glu Lys Ser Lys Leu Asp Asp Lys Asp Tyr Ile Glu Lys Gly Ile
        370                 375                 380 gca atc aat gat aat gta cag aaa gaa gat gtg gtg ttg tgt gaa agt    1322
Ala Ile Asn Asp Asn Val Gln Lys Glu Asp Val Val Leu Cys Glu Ser
            385                 390                 395 gtc caa aaa ggg ttg gaa aca cca gca tat cgt agt gga aga tat gtg    1370
Val Gln Lys Gly Leu Glu Thr Pro Ala Tyr Arg Ser Gly Arg Tyr Val
    400                 405                 410 atg cca att gag aaa gga atc cat cat ttc cac tgc tgg ttg cac caa    1418
Met Pro Ile Glu Lys Gly Ile His His Phe His Cys Trp Leu His Gln
415                 420                 425                 430 gta ttg aag tgattgcagc agatcatcag atgttcgttt cttcttgtat            1467
Val Leu Lys
```

-continued

```
tggaattgga tattatgatt aataagtaaa attataatgt cataatgtag ttgagattgt    1527
tgctagagtt gagcgtatgc tcctcatgca ctacttagtt atcaagtgtg tatgtctttg    1587
gtcatgggca aaatgtatgt ttcttgctag aatttatata ttatggtgct aatgtccaat    1647
ataaataaaa accatagcac ccctttaatt ccctacttag gtttatatcc catttatttt    1707
cgggggatct atgagataga ttgtctatga acattatttt tcgactcgtg tatggtattc    1767
atcccttgtg tagggtgaag taaacattga gtgtatgaag ttttcattga gtttctgctt    1827
t                                                                   1828
```

<210> SEQ ID NO 2
<211> LENGTH: 433
<212> TYPE: PRT
<213> ORGANISM: Chenopodium album

<400> SEQUENCE: 2

```
Met Ala Ala Ser Ala Thr Thr Met Leu Leu Lys Tyr Pro Thr Thr Val
1               5                   10                  15

Cys Gly Ile Pro Asn Ser Ser Asn Asn Asp Thr Ser Asn Asn Ile
            20                  25                  30

Val Pro Ile Pro Gln Thr Ser Thr Asn Asn Pro Val Leu Lys Phe Arg
        35                  40                  45

Thr Pro Asn Lys Thr Ile Asn Ala Val Ala Ala Pro Ala Phe Pro Ser
    50                  55                  60

Leu Asn Thr Thr Thr Thr Pro Pro Ser Ile Gln Ser Leu Val Gln Glu
65                  70                  75                  80

Phe Asp Pro Lys Ile Pro Ala Lys Asp Ala Leu Thr Pro Pro Ser Ser
                85                  90                  95

Trp Tyr Thr Asp Ala Ala Phe Tyr Ala His Glu Leu Asp Arg Ile Phe
            100                 105                 110

Tyr Lys Gly Trp Gln Val Pro Gly Tyr Ser Asp Gln Ile Lys Glu Pro
        115                 120                 125

Asn Gln Tyr Phe Thr Gly Thr Leu Gly Asn Val Glu Tyr Leu Val Cys
    130                 135                 140

Arg Asp Gly Glu Gly Lys Val His Ala Phe His Asn Val Cys Thr His
145                 150                 155                 160

Arg Ala Ser Ile Leu Ala Cys Gly Ser Gly Lys Lys Ser Cys Phe Val
                165                 170                 175

Cys Pro Tyr His Gly Trp Val Phe Gly Met Asn Gly Ser Leu Thr Lys
            180                 185                 190

Ala Ser Lys Ala Thr Glu Glu Gln Ser Leu Asp Pro Asp Glu Leu Gly
        195                 200                 205

Leu Val Pro Leu Lys Val Ala Val Trp Gly Pro Phe Ile Leu Ile Ser
    210                 215                 220

Leu Asp Arg Ser Ser Leu Glu Val Gly Asp Val Gly Ser Glu Trp Leu
225                 230                 235                 240

Gly Ser Cys Ala Glu Asp Val Lys Ala His Ala Phe Asp Pro Asn Leu
                245                 250                 255

Gln Phe Ile Asn Arg Ser Glu Phe Pro Met Glu Ser Asn Trp Lys Ile
            260                 265                 270

Phe Ser Asp Asn Tyr Leu Asp Ser Ser Tyr His Val Pro Tyr Ala His
        275                 280                 285

Lys Tyr Tyr Ala Thr Glu Leu Asp Phe Asp Thr Tyr Gln Thr Asp Met
    290                 295                 300
```

-continued

```
Ile Gly Asn Val Thr Ile Gln Arg Val Ala Gly Ser Ser Asn Asn Gly
305                 310                 315                 320

Phe Asn Arg Leu Gly Ser Gln Ala Phe Tyr Ala Phe Ala Tyr Pro Asn
            325                 330                 335

Phe Ala Val Glu Arg Tyr Gly Pro Trp Met Thr Thr Met His Ile Leu
        340                 345                 350

Pro Leu Gly Pro Arg Lys Cys Lys Leu Val Val Asp Tyr Tyr Ile Glu
    355                 360                 365

Lys Ser Lys Leu Asp Asp Lys Asp Tyr Ile Glu Lys Gly Ile Ala Ile
370                 375                 380

Asn Asp Asn Val Gln Lys Glu Asp Val Val Leu Cys Glu Ser Val Gln
385                 390                 395                 400

Lys Gly Leu Glu Thr Pro Ala Tyr Arg Ser Gly Arg Tyr Val Met Pro
                405                 410                 415

Ile Glu Lys Gly Ile His His Phe His Cys Trp Leu His Gln Val Leu
            420                 425                 430

Lys
```

<210> SEQ ID NO 3
<211> LENGTH: 1651
<212> TYPE: DNA
<213> ORGANISM: Chenopodium album
<220> FEATURE:
<221> NAME/KEY: CDS
<222> LOCATION: (119)..(1423)
<223> OTHER INFORMATION:

<400> SEQUENCE: 3

```
cttgaattat acaagctaag tatatatatt gttgatcatc tttcatacca cctttaaaaa      60
aaattataac aacaaaagga agtgtttagt tattgcttga tcatcatata atatcaac      118 atg tca gca agt gca aca aca atg ttg ctg aaa tac cca aca act gta      166
Met Ser Ala Ser Ala Thr Thr Met Leu Leu Lys Tyr Pro Thr Thr Val
1               5                   10                  15 tgt ggt ata cca aat tca tca tca aac aat gat act tca aat aac atc      214
Cys Gly Ile Pro Asn Ser Ser Ser Asn Asn Asp Thr Ser Asn Asn Ile
            20                  25                  30 gtc cca att cca caa act agt act aat aat ccg gta ctt aag ttt cgt      262
Val Pro Ile Pro Gln Thr Ser Thr Asn Asn Pro Val Leu Lys Phe Arg
        35                  40                  45 acc cct aat aaa acc att aac gcc gtc gct gcc ccg gct ttt cct tct      310
Thr Pro Asn Lys Thr Ile Asn Ala Val Ala Ala Pro Ala Phe Pro Ser
    50                  55                  60 tta agt acc acc act act ccg ccg tcg att caa tca ctt gtc cag gaa      358
Leu Ser Thr Thr Thr Thr Pro Pro Ser Ile Gln Ser Leu Val Gln Glu
65                  70                  75                  80 ttc gat ccg agg att ctg gcc gag gat gct ctc acg cct cct agc tct      406
Phe Asp Pro Arg Ile Leu Ala Glu Asp Ala Leu Thr Pro Pro Ser Ser
                85                  90                  95 tgg tat act gaa cct gcc ttc tat gct cat gaa ctt gac cgt atc ttt      454
Trp Tyr Thr Glu Pro Ala Phe Tyr Ala His Glu Leu Asp Arg Ile Phe
            100                 105                 110 tac aaa gga tgg caa gtc gca ggg tac agc gat caa att aag gag cct      502
Tyr Lys Gly Trp Gln Val Ala Gly Tyr Ser Asp Gln Ile Lys Glu Pro
        115                 120                 125 aac caa tat ttc acc gga acg tta gga aat gtt gaa tat ttg gtg tgt      550
Asn Gln Tyr Phe Thr Gly Thr Leu Gly Asn Val Glu Tyr Leu Val Cys
    130                 135                 140 cga gat ggt gaa gga aaa gtt cat gca ttt cac aat gtt tgc act cat      598
```

```
Arg Asp Gly Glu Gly Lys Val His Ala Phe His Asn Val Cys Thr His
145                 150                 155                 160 cgt gct tcg att ctt gct tgt gga agt ggc aaa aaa tcg tgt ttc gta     646
Arg Ala Ser Ile Leu Ala Cys Gly Ser Gly Lys Lys Ser Cys Phe Val
                165                 170                 175 tgc cct tac cat ggt tgg gta ttt ggc atg aat gga tca ctt acg aaa     694
Cys Pro Tyr His Gly Trp Val Phe Gly Met Asn Gly Ser Leu Thr Lys
            180                 185                 190 gct tcc aaa gca acc gaa gaa cag tcc ctt gat ccc gat gaa ctt ggg     742
Ala Ser Lys Ala Thr Glu Glu Gln Ser Leu Asp Pro Asp Glu Leu Gly
        195                 200                 205 ctt gta ccc ctg aaa gtt gca gta tgg ggc cca ttt ata ctc atc agt     790
Leu Val Pro Leu Lys Val Ala Val Trp Gly Pro Phe Ile Leu Ile Ser
    210                 215                 220 ttg gac aga tca agc ctt gaa gta ggc gat gtt gga tct gaa tgg ctt     838
Leu Asp Arg Ser Ser Leu Glu Val Gly Asp Val Gly Ser Glu Trp Leu
225                 230                 235                 240 ggt agt tgt gct gaa gat gtt aag gcc cat gct ttt gac cct aat ttg     886
Gly Ser Cys Ala Glu Asp Val Lys Ala His Ala Phe Asp Pro Asn Leu
                245                 250                 255 cag ttc atc aat agg agt gaa ttt cca atg gaa tct aat tgg aag att     934
Gln Phe Ile Asn Arg Ser Glu Phe Pro Met Glu Ser Asn Trp Lys Ile
            260                 265                 270 ttc agt gac aac tac ttg gat agc tcg tac cat gtt cct tat gca cac     982
Phe Ser Asp Asn Tyr Leu Asp Ser Ser Tyr His Val Pro Tyr Ala His
        275                 280                 285 aag tac tat gca act gaa ctc gac ttt gat act tat caa acc gat atg     1030
Lys Tyr Tyr Ala Thr Glu Leu Asp Phe Asp Thr Tyr Gln Thr Asp Met
    290                 295                 300 att gga aat gtc acg att caa aga gtg gcg ggg agt tca aac aag cca     1078
Ile Gly Asn Val Thr Ile Gln Arg Val Ala Gly Ser Ser Asn Lys Pro
305                 310                 315                 320 gat ggt ttt gat aga ctt gga tct caa gca ttc tat gct ttt gca tac     1126
Asp Gly Phe Asp Arg Leu Gly Ser Gln Ala Phe Tyr Ala Phe Ala Tyr
                325                 330                 335 cct aac ttt gct gtg gaa agg tat ggc cct tgg atg aca aca atg cat     1174
Pro Asn Phe Ala Val Glu Arg Tyr Gly Pro Trp Met Thr Thr Met His
            340                 345                 350 att ctt cca tta gga cca aga aaa tgc aaa tta gtg gtg gac tac tat     1222
Ile Leu Pro Leu Gly Pro Arg Lys Cys Lys Leu Val Val Asp Tyr Tyr
        355                 360                 365 att gaa aaa tca atg ctg gac gac aag gat tac atc gag aag ggc ata     1270
Ile Glu Lys Ser Met Leu Asp Asp Lys Asp Tyr Ile Glu Lys Gly Ile
    370                 375                 380 gca atc aat gat aat gta cag aaa gaa gat gtg gtg ttg tgt gaa agt     1318
Ala Ile Asn Asp Asn Val Gln Lys Glu Asp Val Val Leu Cys Glu Ser
385                 390                 395                 400 gtc caa aaa ggg ttg gag aca cca gca tat cgt agt gga aga tat gtg     1366
Val Gln Lys Gly Leu Glu Thr Pro Ala Tyr Arg Ser Gly Arg Tyr Val
                405                 410                 415 atg cca att gag aaa gga atc cat cat ttc cac tgt tgg ttc cac caa     1414
Met Pro Ile Glu Lys Gly Ile His His Phe His Cys Trp Phe His Gln
            420                 425                 430 gta ttg aag tgatagcagc agatcagatg ttcgtttctt aatttccttt             1463
Val Leu Lys
        435 tattggaact ggataattat aataataata agtaaaaaag taaaattata atgtcatgta   1523 gttgagattg ttgctagagt tgagcgtatg ctcctcatgc acttagttat caagtgtgta   1583
```

```
tgtgtttggt catggacaaa atgtttcttg ctagaattta tcatattata aggtgctaat    1643
gtccaata                                                             1651
```

<210> SEQ ID NO 4
<211> LENGTH: 435
<212> TYPE: PRT
<213> ORGANISM: Chenopodium album

<400> SEQUENCE: 4

```
Met Ser Ala Ser Ala Thr Thr Met Leu Leu Lys Tyr Pro Thr Thr Val
1               5                   10                  15

Cys Gly Ile Pro Asn Ser Ser Asn Asp Thr Ser Asn Asn Ile
            20                  25                  30

Val Pro Ile Pro Gln Thr Ser Thr Asn Asn Pro Val Leu Lys Phe Arg
            35                  40                  45

Thr Pro Asn Lys Thr Ile Asn Ala Val Ala Pro Ala Phe Pro Ser
    50                  55                  60

Leu Ser Thr Thr Thr Pro Pro Ser Ile Gln Ser Leu Val Gln Glu
65                  70                  75                  80

Phe Asp Pro Arg Ile Leu Ala Glu Asp Ala Leu Thr Pro Pro Ser Ser
                85                  90                  95

Trp Tyr Thr Glu Pro Ala Phe Tyr Ala His Glu Leu Asp Arg Ile Phe
            100                 105                 110

Tyr Lys Gly Trp Gln Val Ala Gly Tyr Ser Asp Gln Ile Lys Glu Pro
            115                 120                 125

Asn Gln Tyr Phe Thr Gly Thr Leu Gly Asn Val Glu Tyr Leu Val Cys
    130                 135                 140

Arg Asp Gly Glu Gly Lys Val His Ala Phe His Asn Val Cys Thr His
145                 150                 155                 160

Arg Ala Ser Ile Leu Ala Cys Gly Ser Gly Lys Lys Ser Cys Phe Val
                165                 170                 175

Cys Pro Tyr His Gly Trp Val Phe Gly Met Asn Gly Ser Leu Thr Lys
            180                 185                 190

Ala Ser Lys Ala Thr Glu Glu Gln Ser Leu Asp Pro Asp Glu Leu Gly
            195                 200                 205

Leu Val Pro Leu Lys Val Ala Val Trp Gly Pro Phe Ile Leu Ile Ser
    210                 215                 220

Leu Asp Arg Ser Ser Leu Glu Val Gly Asp Val Gly Ser Glu Trp Leu
225                 230                 235                 240

Gly Ser Cys Ala Glu Asp Val Lys Ala His Ala Phe Asp Pro Asn Leu
                245                 250                 255

Gln Phe Ile Asn Arg Ser Glu Phe Pro Met Glu Ser Asn Trp Lys Ile
            260                 265                 270

Phe Ser Asp Asn Tyr Leu Asp Ser Ser Tyr His Val Pro Tyr Ala His
            275                 280                 285

Lys Tyr Tyr Ala Thr Glu Leu Asp Phe Asp Thr Tyr Gln Thr Asp Met
    290                 295                 300

Ile Gly Asn Val Thr Ile Gln Arg Val Ala Gly Ser Ser Asn Lys Pro
305                 310                 315                 320

Asp Gly Phe Asp Arg Leu Gly Ser Gln Ala Phe Tyr Ala Phe Ala Tyr
                325                 330                 335

Pro Asn Phe Ala Val Glu Arg Tyr Gly Pro Trp Met Thr Thr Met His
            340                 345                 350

Ile Leu Pro Leu Gly Pro Arg Lys Cys Lys Leu Val Val Asp Tyr Tyr
```

|     |     |     |     |     |     |     |     |     |     |     |     |     |
| --- | --- | --- | --- | --- | --- | --- | --- | --- | --- | --- | --- | --- |
|     |     |     | 355 |     |     |     | 360 |     |     |     | 365 |     |
| Ile | Glu | Lys | Ser | Met | Leu | Asp | Asp | Lys | Asp | Tyr | Ile | Glu | Lys | Gly | Ile |
|     | 370 |     |     |     | 375 |     |     |     |     | 380 |     |     |
| Ala | Ile | Asn | Asp | Asn | Val | Gln | Lys | Glu | Asp | Val | Val | Leu | Cys | Glu | Ser |
| 385 |     |     |     | 390 |     |     |     |     | 395 |     |     |     |     | 400 |
| Val | Gln | Lys | Gly | Leu | Glu | Thr | Pro | Ala | Tyr | Arg | Ser | Gly | Arg | Tyr | Val |
|     |     |     |     | 405 |     |     |     |     | 410 |     |     |     |     | 415 |
| Met | Pro | Ile | Glu | Lys | Gly | Ile | His | His | Phe | His | Cys | Trp | Leu | His | Gln |
|     |     |     | 420 |     |     |     |     | 425 |     |     |     |     | 430 |     |
| Val | Leu | Lys |
|     |     | 435 |

<210> SEQ ID NO 5
<211> LENGTH: 1712
<212> TYPE: DNA
<213> ORGANISM: Chenopodium album
<220> FEATURE:
<221> NAME/KEY: CDS
<222> LOCATION: (133)..(1431)
<223> OTHER INFORMATION:

<400> SEQUENCE: 5

```
cttgaattac acaagctaag ttaagctaag ctatattgtt gatcatcttt cataccacct      60
cctttaaaaa aaaaaaatta taacaacaaa aggaagtgtt tagttattgc ttgatcatca     120
tataacatca at atg gca gca agt gca aca aca atg ttg ctg aaa tac cca    171
              Met Ala Ala Ser Ala Thr Thr Met Leu Leu Lys Tyr Pro
              1               5                   10 aca act gta tgt ggt ata cca aat tca tca tca aac aat gat act tca     219
Thr Thr Val Cys Gly Ile Pro Asn Ser Ser Ser Asn Asn Asp Thr Ser
      15                  20                  25 aat aac atc gtc cca att cca caa act att act aat aat ccg gta ctt    267
Asn Asn Ile Val Pro Ile Pro Gln Thr Ile Thr Asn Asn Pro Val Leu
 30                  35                  40                  45 aag ttt cgt acc cct aat aaa acc att aac gcc gtc gct gcc ccg gct    315
Lys Phe Arg Thr Pro Asn Lys Thr Ile Asn Ala Val Ala Ala Pro Ala
                 50                  55                  60 ttt cct tct tta aac acc acc act act ccg ccg tca att caa tca ctt    363
Phe Pro Ser Leu Asn Thr Thr Thr Thr Pro Pro Ser Ile Gln Ser Leu
             65                  70                  75 gtc cag gaa ttc gat ccg agg att ccg gcc gag gat gct ctt acg cct    411
Val Gln Glu Phe Asp Pro Arg Ile Pro Ala Glu Asp Ala Leu Thr Pro
         80                  85                  90 cct agc tct tgg tat act gaa cct gct ttc tat gct cat gaa ctt gac    459
Pro Ser Ser Trp Tyr Thr Glu Pro Ala Phe Tyr Ala His Glu Leu Asp
     95                  100                 105 cgt atc ttt tac aag gga tgg caa gtc gca ggg tac agt gat caa att    507
Arg Ile Phe Tyr Lys Gly Trp Gln Val Ala Gly Tyr Ser Asp Gln Ile
110                 115                 120                 125 aag gag cct aac caa tat ttc acc gga acg tta gga aat gtt gaa tat    555
Lys Glu Pro Asn Gln Tyr Phe Thr Gly Thr Leu Gly Asn Val Glu Tyr
                 130                 135                 140 ttg gtg tgt cga gat ggt gaa ggt aaa gtt cat gca ttt cac aac gtt    603
Leu Val Cys Arg Asp Gly Glu Gly Lys Val His Ala Phe His Asn Val
             145                 150                 155 tgc acc cat cgt gct tcg att ctt gct tgt gga agc gga aaa aaa tcg    651
Cys Thr His Arg Ala Ser Ile Leu Ala Cys Gly Ser Gly Lys Lys Ser
         160                 165                 170 tgt ttt gta tgc cct tac cat gga tgg gta ttt ggc atg aat gga tcg    699
Cys Phe Val Cys Pro Tyr His Gly Trp Val Phe Gly Met Asn Gly Ser
     175                 180                 185
```

```
                  175                 180                 185
ctt aca aaa gct tcc aaa gca agc gaa gaa cag tca ctt gat ccc gat        747
Leu Thr Lys Ala Ser Lys Ala Ser Glu Glu Gln Ser Leu Asp Pro Asp
190                 195                 200                 205 gaa ctt ggg ctt gta ccc ctg aaa gtt gca gta tgg ggc cca ttt ata        795
Glu Leu Gly Leu Val Pro Leu Lys Val Ala Val Trp Gly Pro Phe Ile
                    210                 215                 220 ctc atc agt ttg gac aga tca agc ctt gaa gta gat gat gtt gga tct        843
Leu Ile Ser Leu Asp Arg Ser Ser Leu Glu Val Asp Asp Val Gly Ser
                225                 230                 235 gaa tgg ctt ggt agt tgt gct gaa gat gtt aag gcc cat gct ttt gac        891
Glu Trp Leu Gly Ser Cys Ala Glu Asp Val Lys Ala His Ala Phe Asp
            240                 245                 250 cct aat ttg cag ttc atc aat agg agt gaa ttt cca atg gaa tct aat        939
Pro Asn Leu Gln Phe Ile Asn Arg Ser Glu Phe Pro Met Glu Ser Asn
        255                 260                 265 tgg aag att ttc agt gac aac tat ttg gat agc tcg tac cat gtt cct        987
Trp Lys Ile Phe Ser Asp Asn Tyr Leu Asp Ser Ser Tyr His Val Pro
270                 275                 280                 285 tat gca cac aag tac tat gct act gaa ctc gac ttt gat act tac caa        1035
Tyr Ala His Lys Tyr Tyr Ala Thr Glu Leu Asp Phe Asp Thr Tyr Gln
                    290                 295                 300 act gat atg atc gga aat gtc acg att caa aga gtg gca ggg agt tca        1083
Thr Asp Met Ile Gly Asn Val Thr Ile Gln Arg Val Ala Gly Ser Ser
                305                 310                 315 aac aat ggt ttt aat aga ctt gga tct caa gca ttc tac gct ttt gca        1131
Asn Asn Gly Phe Asn Arg Leu Gly Ser Gln Ala Phe Tyr Ala Phe Ala
            320                 325                 330 tac cct aac ttt gct gtg gaa agg tat ggc cct tgg atg aca aca atg        1179
Tyr Pro Asn Phe Ala Val Glu Arg Tyr Gly Pro Trp Met Thr Thr Met
        335                 340                 345 cac att ctt cca tta gga cca agg aaa tgc aaa tta gtg gtg gac tac        1227
His Ile Leu Pro Leu Gly Pro Arg Lys Cys Lys Leu Val Val Asp Tyr
350                 355                 360                 365 tat att gaa aaa tca aag ctg gac gac aag gat tac atc gag aag ggc        1275
Tyr Ile Glu Lys Ser Lys Leu Asp Asp Lys Asp Tyr Ile Glu Lys Gly
                    370                 375                 380 ata gca atc aat gat aat gta cag aaa gaa gat gtg gtg ttg tgt gaa        1323
Ile Ala Ile Asn Asp Asn Val Gln Lys Glu Asp Val Val Leu Cys Glu
                385                 390                 395 agt gtc caa aaa ggg ttg gag aca cct gcg tat cgt agt gga aga tat        1371
Ser Val Gln Lys Gly Leu Glu Thr Pro Ala Tyr Arg Ser Gly Arg Tyr
            400                 405                 410 gtg atg cca att gag aaa gga atc cat cat ttc cac tgt tgg ttg cac        1419
Val Met Pro Ile Glu Lys Gly Ile His His Phe His Cys Trp Leu His
        415                 420                 425 caa gta ttg aag tgattgcagc agatcagatg ttcgtttctt aatttccttt          1471
Gln Val Leu Lys
430 tattggaatt ggatgattgt tataataata agtaaaatta taatgtcatg tagttgagat      1531 tgttgctaga gttgagcgta tgctcctcat gcacttagtt atcaagtgtg tatgtgtttg      1591 gtcatgggca aaatgtattt tcttgctaga atttgttata ttatggtgct aatgtccaat      1651 aatataaata acaccattgc accctttccc tacttgagaa attatatccc atttatttc       1711 g                                                                     1712

<210> SEQ ID NO 6
<211> LENGTH: 433
```

```
<212> TYPE: PRT
<213> ORGANISM: Chenopodium album

<400> SEQUENCE: 6

Met Ala Ala Ser Ala Thr Thr Met Leu Leu Lys Tyr Pro Thr Thr Val
1               5                   10                  15

Cys Gly Ile Pro Asn Ser Ser Asn Asn Asp Thr Ser Asn Asn Ile
            20                  25                  30

Val Pro Ile Pro Gln Thr Ile Thr Asn Asn Pro Val Leu Lys Phe Arg
            35                  40                  45

Thr Pro Asn Lys Thr Ile Asn Ala Val Ala Ala Pro Ala Phe Pro Ser
    50                  55                  60

Leu Asn Thr Thr Thr Thr Pro Pro Ser Ile Gln Ser Leu Val Gln Glu
65                  70                  75                  80

Phe Asp Pro Arg Ile Pro Ala Glu Asp Ala Leu Thr Pro Pro Ser Ser
                85                  90                  95

Trp Tyr Thr Glu Pro Ala Phe Tyr Ala His Glu Leu Asp Arg Ile Phe
                100                 105                 110

Tyr Lys Gly Trp Gln Val Ala Gly Tyr Ser Asp Gln Ile Lys Glu Pro
            115                 120                 125

Asn Gln Tyr Phe Thr Gly Thr Leu Gly Asn Val Glu Tyr Leu Val Cys
    130                 135                 140

Arg Asp Gly Glu Gly Lys Val His Ala Phe His Asn Val Cys Thr His
145                 150                 155                 160

Arg Ala Ser Ile Leu Ala Cys Gly Ser Gly Lys Lys Ser Cys Phe Val
                165                 170                 175

Cys Pro Tyr His Gly Trp Val Phe Gly Met Asn Gly Ser Leu Thr Lys
                180                 185                 190

Ala Ser Lys Ala Ser Glu Glu Gln Ser Leu Asp Pro Asp Glu Leu Gly
            195                 200                 205

Leu Val Pro Leu Lys Val Ala Val Trp Gly Pro Phe Ile Leu Ile Ser
    210                 215                 220

Leu Asp Arg Ser Ser Leu Glu Val Asp Asp Val Gly Ser Glu Trp Leu
225                 230                 235                 240

Gly Ser Cys Ala Glu Asp Val Lys Ala His Ala Phe Asp Pro Asn Leu
                245                 250                 255

Gln Phe Ile Asn Arg Ser Glu Phe Pro Met Glu Ser Asn Trp Lys Ile
                260                 265                 270

Phe Ser Asp Asn Tyr Leu Asp Ser Ser Tyr His Val Pro Tyr Ala His
            275                 280                 285

Lys Tyr Tyr Ala Thr Glu Leu Asp Phe Asp Thr Tyr Gln Thr Asp Met
    290                 295                 300

Ile Gly Asn Val Thr Ile Gln Arg Val Ala Gly Ser Ser Asn Asn Gly
305                 310                 315                 320

Phe Asn Arg Leu Gly Ser Gln Ala Phe Tyr Ala Phe Ala Tyr Pro Asn
                325                 330                 335

Phe Ala Val Glu Arg Tyr Gly Pro Trp Met Thr Thr Met His Ile Leu
                340                 345                 350

Pro Leu Gly Pro Arg Lys Cys Lys Leu Val Val Asp Tyr Tyr Ile Glu
            355                 360                 365

Lys Ser Lys Leu Asp Asp Lys Asp Tyr Ile Glu Lys Gly Ile Ala Ile
    370                 375                 380

Asn Asp Asn Val Gln Lys Glu Asp Val Val Leu Cys Glu Ser Val Gln
385                 390                 395                 400
```

Lys Gly Leu Glu Thr Pro Ala Tyr Arg Ser Gly Arg Tyr Val Met Pro
            405                 410                 415

Ile Glu Lys Gly Ile His His Phe His Cys Trp Leu His Gln Val Leu
            420                 425                 430

Lys

<210> SEQ ID NO 7
<211> LENGTH: 23
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (9)..(9)
<223> OTHER INFORMATION: n is a, g, c, or t
<221> NAME/KEY: misc_feature
<222> LOCATION: (15)..(15)
<223> OTHER INFORMATION: n is a, g, c, or t
<221> NAME/KEY: misc_feature
<222> LOCATION: (18)..(18)
<223> OTHER INFORMATION: n is a, g, c, or t

<400> SEQUENCE: 7
tggtayacng arccngcntt yta                                     23

<210> SEQ ID NO 8
<211> LENGTH: 26
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (9)..(9)
<223> OTHER INFORMATION: n is a, g, c, or t
<221> NAME/KEY: misc_feature
<222> LOCATION: (15)..(15)
<223> OTHER INFORMATION: n is a, g, c, or t
<221> NAME/KEY: misc_feature
<222> LOCATION: (18)..(18)
<223> OTHER INFORMATION: n is a, g, c, or t

<400> SEQUENCE: 8
tayttrtgng crtanggnac rtgrta                                  26

<210> SEQ ID NO 9
<211> LENGTH: 24
<212> TYPE: DNA
<213> ORGANISM: Artificial Sequence
<220> FEATURE:
<223> OTHER INFORMATION: Synthetic DNA

<400> SEQUENCE: 9
gtgcattgtt gtcatccaag ggcc                                    24

<210> SEQ ID NO 10
<211> LENGTH: 28
<212> TYPE: DNA
<213> ORGANISM: Artificial Sequence
<220> FEATURE:
<223> OTHER INFORMATION: Synthetic DNA

<400> SEQUENCE: 10
gatcccgatg aacttgggct tgtacccc                                28

<210> SEQ ID NO 11
<211> LENGTH: 26
<212> TYPE: DNA

-continued

```
<213> ORGANISM: Artificial Sequence
<220> FEATURE:
<223> OTHER INFORMATION: Synthetic DNA

<400> SEQUENCE: 11
cccgggttta gttattgctt gatcat                                              26

<210> SEQ ID NO 12
<211> LENGTH: 26
<212> TYPE: DNA
<213> ORGANISM: Artificial Sequence
<220> FEATURE:
<223> OTHER INFORMATION: Synthetic DNA

<400> SEQUENCE: 12
gagctcctgc aatcacttca atactt                                              26

<210> SEQ ID NO 13
<211> LENGTH: 24
<212> TYPE: DNA
<213> ORGANISM: Artificial Sequence
<220> FEATURE:
<223> OTHER INFORMATION: Synthetic DNA

<400> SEQUENCE: 13
taatggatcc attaacgccg tcgc                                                24

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14
gggtaccaat cacttcaata cttgg                                               25

<210> SEQ ID NO 15
<211> LENGTH: 26
<212> TYPE: DNA
<213> ORGANISM: Artificial Sequence
<220> FEATURE:
<223> OTHER INFORMATION: Synthetic DNA

<400> SEQUENCE: 15
cccgggaaaa ccattatggc cgtcgc                                              26

<210> SEQ ID NO 16
<211> LENGTH: 127
<212> TYPE: DNA
<213> ORGANISM: Artificial Sequence
<220> FEATURE:
<223> OTHER INFORMATION: Synthetic DNA
<221> NAME/KEY: CDS
<222> LOCATION: (1)..(126)
<223> OTHER INFORMATION:

<400> SEQUENCE: 16 atg gca gca agt gca aca aca atg ttg ctg aaa tac cca aca act gta           48
Met Ala Ala Ser Ala Thr Thr Met Leu Leu Lys Tyr Pro Thr Thr Val
1               5                   10                  15 tgt ggt ata cca aat tca tca tca aac aat gat act tca aat aac atc           96
Cys Gly Ile Pro Asn Ser Ser Ser Asn Asn Asp Thr Ser Asn Asn Ile
            20                  25                  30
```

```
                                                        -continued gtc cca att cca caa act att act aat aat c                                127
Val Pro Ile Pro Gln Thr Ile Thr Asn Asn
         35                      40

<210> SEQ ID NO 17
<211> LENGTH: 42
<212> TYPE: PRT
<213> ORGANISM: Artificial Sequence
<220> FEATURE:
<223> OTHER INFORMATION: Synthetic DNA

<400> SEQUENCE: 17

Met Ala Ala Ser Ala Thr Thr Met Leu Leu Lys Tyr Pro Thr Thr Val
1               5                  10                  15

Cys Gly Ile Pro Asn Ser Ser Ser Asn Asn Asp Thr Ser Asn Asn Ile
            20                  25                  30

Val Pro Ile Pro Gln Thr Ile Thr Asn Asn
         35                      40
```

CHOLINE MONOOXYGENASE GENE

BACKGROUND OF THE INVENTION

1. Field of the Invention

The present invention relates to plant choline monooxygenase which is involved in the occurence of plant injury attributable to dry or saline soil, which is believed to contribute to the improve of plant tolerance to dry or saline soil, and which is induced by dry or saline soil, as well as a gene encoding the choline monooxygenae.

2. Descriptionof the Related Art

At presnt, desertification or salt accumulation in cultivated land is progressing in a large is number of areas on the earth. These envinmental changes considered as serious issues in connection with current envirormental problems and food problems in the 21st century. As means to solve these problems, the breeding of environmental stress-resistant plants is attracting attentiou together with engineering-based solutions as irrigation.

Specific examples of damage caused by salt acmulafn may be enumerated as follows: (1) because of accumulated salts in soil, moisture potential in soil decems, which makes it impossibe for plants to absorb moisture; (2) because of salts which have been absorbed (or which have invaded) into plant bodies plant metabolism is disturbed; and (3) becuse of accumulated salts, absorption of other ions necessary for plant growth is inhibited (Fumihiko Sato, Plant Cell Engineering, an extra issue, "Envirnmental Problems and Bioology", pp. 33–39, 1994). In particular, inhibition of moisture absorption caused by dehydration, salt injury, etc. eventually decreases photosynthesis activity to thereby inhibit the growth of plants The existence of adaptation mianisms against stresses such as dehydration or salts has become evident in microorganisms and plants. Among all, compatible solutes (i.e. low molecular weight orgaic compounds or osmoregulating substances) have been investigated vigorously. Compatible solutes are those substances which are characterized by having low molecular weights, being rich in water-solubility and difficult to metbolize, and not affecting metabolismn. As specific examples of compatible solutes, amphoteric compounds such as glycine betaine, proline, and polyols such as pinitol, sorbitol, mannitol are known. In particular, glycine betain (hereinafter, referred to as "betaine") is utlized widely not only in higher plants such as chenopodiaccous plants gramineous plants and solanaceous plants, but also in microorganism. It is noted that this compatible solute is functioning in protecting proteins from high temperature stress (Paleg, L. G., et al., Aust. J. Plant Physiol. 8:107–114, 1981; Allakhdverdiev S. I., J. Photochem. Pbotoiol. 34:149157, 1996), in maintaining osmotic pressure balance against the environment (Robinson, S. P. and Jones, G. P., Aust. J. Plant Physiol. 13:659–668, 1986) and in protecting soluble enzyes from salt stress (Gabbay-Azaria et al., Arch. Biochem. Biophys. 264:333–339, 1988).

In spinsh which is well studied among higher planis, betaine is syn in two steps through choline and betaine aldehyde. Specifically oxidization in the first step is catalyzed by a ferredoxin-dependent choline monooxygenase (Brouquisse, R. et al., Plant Physiol. 90:322–329, 1989), and oxidization in the second step is catalyzed by a NAD-dependent betaine aldehyde dehydrogenase (Weretilnyk, E. A. et al., Plamta. 178: 342–352, 1999). It is confirmed that when such aplant is exposed to salt stress, the activity of each of the above enzymes rises and the amount of betaine is increased (Hanson, A. D. et al., Proc. Natl. Acid. Sci, U.S.A. 82: 3678–3682, 1985).

A choline oxidase obtained from a Gram-negative soil bacterium, *Arthrobacter globtformis* is able to oxidize choline to betaine in one step oxidiaon (Ikuta S. et al., J. Biochem. 82: 1741–1749, 1977).

Several attempts have been made to accunulate betaine in plants and confer salt tolemace on them by incorporating in plant bodies two enzyme genes from *Escherichia coli* and a higher plant or a choline oxidase gene and allowing the gene constant expression. Accumulation of betaine in plant bodies have been reported when *Arthrobacter globiformis* codA gene (WO96/29857), *E. coli* beta gene (Japanese Unexamined Patent Publicaton No. 10-191983) and spinach CMO gene (Nuccio, M. L. et al., The Plant J., 16: 487–496, 1998) weme incorporated However, no attempts have succeeded in accumulating betaine at such levels as seen in salt tolent plants. Thus, it is desired to establish a betaine synthesis system which can accumulate betaine in plants at high levels.

OBJECTS AND SUMMARY OF THE INVENTION

It is the object of the invention to provide a choline monooxygenase, a gene encoding the same, a vector comprising the gene, a transformmt comprising the vector, a stress resistant plan and a method for inducing betaine accumulation.

As a result of intensive and extensive researches toward the solution of the above problem, the present inventors have isolated a full-length choline monooxygenae gene inducible by dry and saline soil from *Chenopodium album* L. which exhibits tolerance to dry and saline soil and can accumulate betaine at a high rate of about 60 $\mu$mol/g fresh weight under salt stress, and found that this gene is capable of acumulating betaine in plant bodies. Also, the inventors have found for the first time that a transit peptide sequence of the choline monooxygenase gene induces protein accumulation umder salt stress. Thus, the present invention has been achieved.

The present invention relates to the following reombinant protein (a) or (b):

(a) a protein comprising the amino acid sequence shown in SEQ ID NO: 2, 4 or 6;

(b) a protein which comprises the amino acid sequence shown in SEQ ID NO: 2, 4 or 6 having deletion, substitution or addition of one or several amino acids, and which has choline monooxygenase activity.

The present invention further relates to a choline monooxygenase gene encoding the above described protein.

The present invention further relates to a gene comprising the following DNA (c) or (d)

(c) a DNA comprising the nucleotide sequence shown in SEQ ID NO: 1, 3 or 5;

(d) a DNA which hybridizes to a DNA cormprising the nuclcotide sequence shown in SEQ ID NO: 1, 3 or 5 under stringent conditions and which encodes a protein having choline monooxygenase activity.

The present invention fuiwr relates to a recombinant vector comprising the above described gene.

The present invention further relates to a recombinant comprising the above-described recombinant vector.

The present invention further relates to a method for producing a choline monooxygenae comprising culturing the above-described transformant and recovering the choline monooxygenase from the resultant culture.

The present invention further relates to the following peptide (e) or (f):

(e) a peptide comprismg the amino adid sequence shown in SEQ ID NO: 17;

(f) a peptide which comprises the amino acid sequence shown in SEQ ID NO: 17 having deletion, substitution or addition of one or several amino acids and which has signal peptide activity; or a salt thereof.

The present invention further relates to a gene encoding the above-described peptide. Specific examples of the gene include a gene comprising the foUowing DNA (g) or (h):

(g) a DNA comsing thw nucleotide sequenc shown in SEQ ID NO: 16;

(h) a DNA which hybridizes to a DNA comprising the nucleotide sequence shown in SEQ ID NO: 16 under stringent conditions and which encodes a protein having signal peptide activity.

The present invention fisrher relates to a recombinant vector comprising a gene encoding the above-described peptide and a gene of interest. As the gene of interest, a gene which leads to production of a polypeptide or production of a plant metabolite (e.g. a substance that confers stress resistance), or *Chenopodium album* choline monooxygenase gene may be enumerated.

The present invention further relates to a transformant comprising the recombinant vector comprising a gene encoding the above-discribed peptide and a gene of intrest. Specific examples of the transformant include a plant body, plant organ, plant tissue and cultured plant cell.

The present invention further relates to a method for creating an enviernmental stress-resistant plant, comprising culturing or cultivating a transformed plant comprising the above-described recombinant vector under environmental stress (e.g. salt stress) conditions; or an environmental stress-resistant plant created by this method.

The present invention further relates to a method for inducing accumulation of a polypeptide or a plant metabolite (e.g. a subslance that confers envronmental stress resistance), or cultivating the above-described transfromant under environmental stress conditions. As a specific example of the substance that confers environmental stres reistance, betaine may be given.

The present invention further relates to a method for producing betaine, comprising culturing or cultivating a transformant comprising the recombinant vector comprising a gene econcoding the above-described peptide and a choline nonooxygenase gene and then recovering betaine from the resultant culture or the cultivated product.

This speccation includes part or all of the contents as disclosed in the specification and or drawings of Japanese Patent Application No.11-273275, which is a priority document of the present application.

DETAILED DESCRIPTION OF THE INVENTION

Figure 1:
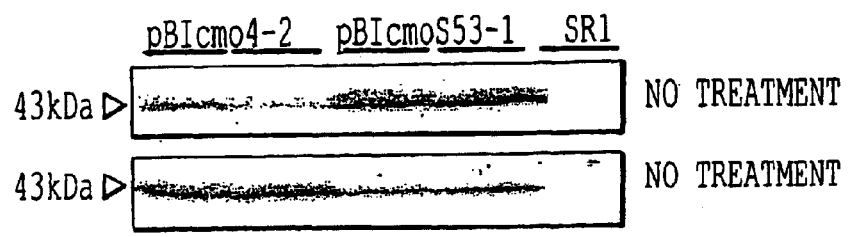
FIG. 1 is a diagram showing the responsivity of a choline moooxygenae (CMO) transit peptide to salt stress.

Hereinbelow, the present invention will be described in detail.

The present invention relates to plant choline monooxygenase gene which is induced by dry and saline soil. As one example of such a gene, *Chenopodium album* choline monooxygewise gene will be described. However, it is believed that other choline monooxygenase genes inducible by dry and saline soil exist in other plant species which, like *Chenopodium album*, exhibit tolerance to dry and saline soil Thus, choline monooxygenase genes derived from plants other than *Chenopodium album* are also included in the gene of the invention.

The choline monooxygenase of the invention comprises the amino acid sequence shown in SEQ ID NO: 2, 4 or 6. However, these amino acid sequences may have soine difference among plant varieties. Also, even in the sae plant variety, the amino acid sequence of choline monooxygenase may be varied because of muttions or the like. Accordingly, a protin which comrpises the amnio acid sequence shown in SEQ ID NO: 2, 4 or 6 havin deletion, substitution or addition of one or seveal (e.g. one to ten) amino acids, and which has choline monooxygense activity is also included in the pxesnt invention.

Further, the present invention provides a choline monooxygenase gene comprising the nucleotide sequence shown in SEQ ID NO: 1, 3 or 5. However, the gene of the invention is not limited to these genes but includes all of the genes encoding the amino acid sequence shown in SEQ ID NO: 2, 4 or 6. The gene of invention also inludes all of the genes encoding a substantial choline monooxygenase comprising the amino acid sequence shown in SEQ ID NO: 2, 4 or 6 having substitution, deletion or addition of one or several (e.g. one to ten) amino acids.

1. Cloning of the Gene of the Invention

The gene of the invention can be isolated by extracting RNA from a plant loaded with stress (e.g. dehydration or salt trearnent) and then subjecting the resultant RNA to RT-PCR. Specific examples of plants which may be used as a source of mRNA include, but are not limited to, chenopodiaceous plants to which *Chenopodium album* belongs. Thepreparation of mRNA may be performed by conventional methods. For example, total RNA may be extracted from the above-mentioned source by the guanidium thiocyanate-cesium chloride medod or the like, and then poly(A)+ RNA (mRNA) may be obtained therefrom by affinity column method using oligo dT-cellulose or poly U-Sepharose or batch method. The poly(A)+ RNA may be fractionated further by sucrose gradient centrifugation or the like. Using the thus obtained mRNAs a template, single-strnded cDNA is synthesized with oligo dT primers and a reverse transcriptase. Then, double-stranded cDNA is synthesized from the single-stranded cDNA. As a pair of primers to be used in RT-PCR. oligonucleotides corresponding to two portions of other plants choline monooxygenase which are highly homologous among plant choline monooxygenass may be used (e.g. partial sequences from spinach choline monooxygee).

Further, a cDNA fragmet encoding a part of the cholinc monooxygenasc of intrest is cloned from the cDNA by KR-PCR. From this cDNA fragment, primers for RACE-PCR are prepared. Using ths prime RACE-PCR is performed on a template cDNA to which an adaptor is ligated at both ends (RACE). Thus, a cDNA encoding the full-length of the choline monooxygenase of interest can be obtained. RACE (Rapid Amplification of cDNA Ends) is a method for recovenng the 5' or 3' missing portion of a cDNA rapidly.

More specifically, upon determination of the sequence of the partial cDNA fragment obtainedby RT-PCR, gene specific primers (GSPs) are designed based on the resultant partial cDNA sequence. Gene specific primers are primers necessary for amplifying DNA fragments which are located at 5' and 3' flanig regions of the above-mentioned partial cDNA sequensce and whose sequences are unknown GSP sequences may be selected arbitrily from the above-mentioned partial cDNA sequence.

Subsequently, DNA fragments located on the 5' side (upstream) and the 3' side (downstream) of the above-mentioned partial cDNA ame amplified. Although the sequences of these DNA fragments which serve as templates are unknown, an adaptor sequence is ligated to one end of each fagment. Then, using a primer which hybridizes to the adaptor (termed "adaptor primer (AP)") and the above-described GSP as a pair of primers, the adaptor-ligated cDNA fragment whose sequence is unknown is amplificd.

In the present invention, RACE may be performed using a commercial kit (Marathon™ cDNA Amplification Kit; Clontech).

The nucleotide sequences of the resultant cDNA fragments are determined by a method based on PCR. For example, a reaction is performed using PRISM Sequencing Kit (Perkin Elmer) containing fluorescence dideoxy terminator, followed by deternination of the nucleotide sequence of the resultant product with an autosequenser (e.g. Model ABI 373; Applied Biosystems).

From the thus obtained partial sequence and nucleotide sequences of 5' and 3' RACE prodducs the nucleotide sequence of the full legth cDNA can be obtained by assembling. Briefly, by joining thse fragments at the sites overlapping with each other, the full-length nucleotide sequence containing 5' and 3' ends is obtain.

SEQ ID NOS. 1, 3 and 5 illustrate nucleotide sequsof the gen of the invention SEQ ID NOS: 2, 4 and 6 illuste amino acid sequences of the choline monooxygenase of the ivention. However, as long as a protein comprising one of the above armio acid sequences has choline monooxygenase activity, the amino acid sequence may have variation (such as deletion, substitution or addition) in one or several amino acids.

For example, 1 to 10 amino acids, preferably 1 to 5 amino acids of the amino acid sequence shown in SEQ ID NO: 2, 4 or 6 may be deleted; 1 to 10 amino acids, preferably 1 to 5 amino acids may be added to the amino acid sequence show in SEQ ID NO: 2, 4 or 6; or 1 to 10 amino acids, preferably 1 to 5 amino acids of the amino acid uence shown in SEQ ID NO: 2, 4 or 6 may be substituted with other amino acids.

The term "choline monooxygenase activity" used in the present invention means het activity to catalyze the first step oxidization from choline to betaine aldehyde. The presence or absence of the above dscribed activity of the protein of the invention can be confiumed by adding to a crude extact of a plant a solution containing choline chloride and DCPIP, and measuring changes in absorbance in the resultant reaction solution (Japanese Unexamined Patent PublicationNo. 10-191983).

Further, a DNA which hybridizes to the above described gene under strigent conditions is also included in the gene of the invention. The "stringent conditions" means these conditions under which the so-called specific hybrid is formed but non-specific hybrids are not formed. For example, those conditions under which highly homologous DNAs (i.e. DNAs having 60% homology or more, preferably 80% homology or more) hybridize to each other and DNAs with less homology do not hybridize to each other may be given.

More specifically, stringent conditions means a sodium concentration of 150–900 mM, preferably 600–900 mM, and a temperature of 60–68° C., preferably 65° C.

When genes consisti of the nucleotide sequences shown in SEQ ID NOS: 1, 3 and 5, respectively, are designated type A, type B and type C, there are 97.0% homology been tye A and type B, 98.2% homology between type A and C, and 97.5% homology between type B and type C. Therefore, a gene which compriss a nucleotide sequence having 90%, preftmbly 97% homology or more to type A gene and which encodes a protein having choline monooxygenae activity is also included in the gene of the invention.

Once the nucteotide sequence of the gene of the invention has been determinde, the gene of the invention can be obtained by chemical synthesis, by PCR using the cloned cDNA as a template, or by hybridiion using a DNA fiasnent having the nucleotide sequence, as a probe. Further, a modified DNA encoding the choline monooxygenase way be synthesized by site specific mutagenesis or other techniques.

In order to introduce mutations into genes, known techniques such as the method of Kunkel, the gapped duplex nethod, etc. or techniques based on these me may be used. For example, mutations may be introduced using a mutation introduction kit (eg. Mutant-K or Mutant-G both from Takara) utilizing site specific mutagenesis or LA PCR in vitro Mutagenesis series kits (Takara).

2. Preparation of Recombinant Vectors and Transformmnts (1) Preparation of Recombinant Vectors The recombinant vector of the invention can be obtained by ligating (inserting the gene of the invention to (into) an appropriate vector. The vector into which the gene of the invention is to be inserted is not particularly limited as long as it is replicable in a host. For example, plasmid DNA, phage DNA or the like may be used.

Specific examples of plasmid DNA include *E. coli*-derived plasmid s (e.g. pBR322, pBR325 pUC118,pUC119, etc.), *Bacillus subtils*-deprived plasmids (e.g. pUB110, pTP5, etc.) and yeast-derived plasmids (eg. YEp13, YEp24, YCp50, etc.), and specific examples of phage DNA include λ phage (Charon4A, Charon21A, EMBL3, EMBL4, λgt10, λg11, λZAP, etc.). Furher an animal virus vector such as retrovirus or vaccina viris; or an insect virus vector such as baculovirus may also be used.

For insertion of the gene of the invention into a vector, a method may be employed in which the purified DNA is digested with aproprate restriction enzymes and then inserted into the rcstction site or the multi-cloning site of an approiate vector DNA for ligation.

The gene of the invention should be incorporated into the vector so that the function thereof can manifested. For this pumpose, the vector of the invention may contain, if desired, cis elements such as an enhancer, splicing signal, poly(A) addition signals, selection :. markers, ribosome binding sequences (SD sequences) or the like in addition to a promoter add the gene of the invention. As the selection marker, dihydrofolate rcdctase gene, ampicillin resistance gene neomycin resisace gene or the like may be enumerated.

(2) Preparation of Transformants

The transformant of the invention can be obtained by inoducng the recombinant vector of the invention into a host so that the gene of interest can expressed. The host usefil in the invention is not particularly limited as long as it can express the DNA of the invention Specific examples of the host include Escherichia bacteria such as *Escherichia coli*; Bacillus bacteria such as *Bacilus subtilis*; Psudomonas bacteria such as *Pseudomonas putida*; Rhizobium bacteria such as *Rhizobium melitoti*; yeast such as *Saccharoyces cerevisiae, Shizosaccharomyces pombe*; animal cells such as COS ceUs, CHO cells; or insect cells such as Sf9 cells.

When a bacterium such as *E. coli* is used as the host, the recombinant vector of the invention should be capable of autonomous replication in this microorganisrn and, at the same time, it is preferred that the vector be composed of a promoter, a ribosome binding sequence the gene of the invention and a transcription termination sequence. The vector may also contain a gene(s) to control the promoter.

As *Escherchia* bacteria, *E, coli*DH5 α or Y1090 stain may be used, for example. As Bacillu bactera, *Bacillus subtilis* may be used, for example. However, the present invention is not limited to the bacteria.

As the promoter, any promoter may be used as long as it can direct the expression of the gene of in a host such as *E. coli*. For examle, an *E. coll-* or phage-derived promoter such as upromote promote lac promoter, $P_L$ promoter or $P_R$ promoter may be used An artificially designed and altered promoter such as tac promoter may also be used.

As a method for introducing the recombinant vector into a bacterium, any method of DNA traicr into bactea may be used. For empl a method calciumrions [Cohen, S. N. etal., Proc. Natl. Acad. Sci., USA, 69:2110–2114 (1972)], elecropoumtion or the like may be used.

When yeast is used as the host, *Saccharomyces cervisiae, Schizosaccharomyces pombe, Pichia pastoris* or the like may be used. In this ease, the promoter to be wued is not particularly limited. Any promoter maybe used as long as it can direct the ression of the gene of interest in yeast. For example, ga11 promoters ga110 promoter, heat shock protein promoter, MF α 1 promoter, PH05 promoter, PGK promoct, GAP promoter, ADH promoter, AOX1 promoter or the like may be used.

As a method for introducing the recombinant vector into yeast, any method of DNA transfer into yeast may be used. For example, electroporation [Becker, D. M, Methods Enzymol., 194:182–187 (1990)], the spheroplast method [Hinnen, A. et al., Proc. Natl. Acad. Sci., USA, 75:1929–1933 (1978)], the lithium accate method [Itoh, H, J. Bacteriol., 153:163–168 (1983)] or the liae may be employed.

When an animal cell is used as the host, simian COS-7 or Vero cells, Chinese hamster ovary cells (CHO cells), mouse L cells, rat GH3 cells, human FL cells or the like may be used. As a promoter, SR α promoter, SV40 promoter LTR promoter, CMV promoter or the like may be used. The early gene promoter of human cytomegalovirus may also be used. As a method for introducing the recombiant vecor into the animal cell, electroporation, the calcium phosphate method, lipofection or the like may be employed.

When an insect ccll is used as the host, Sf9 cells or the like may be used. As a method for introducing the recombinant vector into the insect cell, the calcium phosphate method, lipofection, electroporation or hte like may be employed.

When a plant is used as the host, atransformant may be prepared as descirbed below.

In the present invention, a plant to be transformed may be any of the following plant materials: entire plant bodies, plant organs (e.g. leaves, petals, stems, roots, seeds, ect.), plant tissues (e.g. epidermis, phloem, parenchyma, xlern, vasscular bundles, palisade tissues, spongy tillues, etc.) or cultured plant cells. Specific examples of plant species which may be used for transformationinclude, but are not limited to, thoses belonging to the genus *Chenopodiaceae, Solanaceae, Gramineae, Leguminosae, Rosaceae, Compasitae, Liliaeae, Caryophyllaceae, Cururbitaceae, Convolvulaceae* or *Cruciferae*.

The above-described recombinant vector may be introduced into a plant by conventional transformation methods, e.g. th Agrobactrerium method, the particle gun method, PEG method, electropoation, ect. For example, when Agrobacterium method is used, a plant expression vector constructed is transferred into an appropriate Agobacterium strain (e.g. *Agrobacterium tumefaciens* LBA4404), followed by infection of aseptically cultured leaf discs of a host) e.g. tobacco) with this strain according to the leaf disc method (Hirobumi Uchimiya, Operation Manual for Plant Genes, 1990, pp. 27–31, Kohdansha Scientific Co., Ltd., Tokyo). Thus, a transformed tobacco is obtained.

When the particle gun method is used, entire plant bodies, plant organs or plant tissues may be used as they are, or may be used after preperation of pieces of protoplats. The thus prepared samples may be bombarded using a gene transfer apparatus (e.g. PDS-1000; BioRad). Bombardment conditions vary depending on the type of the plant or sampel. Usually, the sample is bombarded under a pressure of about 450–2000 psi and at a distance of 4–12 cm.

When a cultured plant cell is used as the host, transformation is preformed by introducing the recombiant vector thereinto by the particle gun method, electroporation or the like.

Tumor tissues,shoots, hairy roots, etc. resulted from the transformation can be used directly in cell culture, tissue culture or organ culture. Further, they can be regenerated to plant bodies by using conventional plant tissue culture metbods and administering plant hormones (eg. auxin, cytokinin, gibberelin, abscicic acid, ethylene, brasinolide) at appropriate concentratios.

Whether the gene of interst has been integrated into the host or not cane confirmed by PCx, Southern hybridization, Northern hybridization or the like. For example, DNA is prepared from the transformant and then DNA specific primers are designed for PCR. A PCR reaction may be performed under the same conditions as described above in the prepration of plasmids. Subscquently, the amplified product is subjected to agarose gel electrophoaesis, polyacrylamide gel electrohoresis or capillary eletrophoreis and stained with ethidium bromide, SYBR Green solution, etc. By detecting amplified products as a single band, it can be confirmed that the host has been transformned. Alternatively, a PCR faction may be peformed using primers labelled with a fluorescent dye or the like, and, then the amplified product may be detected. Further, a method may be employed in which a PCR amplified product is bound to a solid phase such as a microplate, and then the product is confirmed by fluorescence or enzyme reactions.

3. Production of the Protein of the Invention

The protein of the invention is a protein comprising the amino alcid sequence encoded by the choline monooxygenase gene of the invention; or a protein which comprises the above amino acid sequence having the above-described mutation in a plurality of amino acids and yet which has choline monooxygenase activity. In this specification, the protein of the invention is sometimes called the "choline monooxygenase protein".

The choline monoxygenase protein of the invention can be obtained by culturing the above-described transformant in a medium and recovering the protein from the resultant culture The term "culture" means any of the following materials: culture supernatant, cultured cells or miroorganisms, or disrupted cells or microorganisms.

The culturing of the transformant of the invention is carried out by conventional methods used for culturing hosts.

As a medium for ulturing the transformant obtained from a microorgamsm host such as *E. coli* or yeast, either a natural or synthetic medium may be used as long as it contains carbon sources, nitrogen sources and inorganic salts assimilable by the microorganism and is capable of efficie cultur of the transformant.

As carbon sources, carbohydrte such as glucose, frutose, sucrose, starch; organic acids suh as acetic acid, propionic acid; and alcohols such as ethol propanol may be used As nitrogen sources, ammonium salts of inorganic or or organic acids (e.g. ammonia, ammonium chloride, ammonium suite, ammonium acetate, ammonium phosphate, etc.) and other nitrogen-containing compounds (e.g. Peptone, meat extract, corn steep liquor, ect.) may be used.

As inorganic substances, potassium dihydrogen phophate, dipotassium hydrogen phosphate, magnesium phosphate, magnesium sulfate, sodium chloride, iron(II) sulfate, manganese sulfate, copper sulfate, calcium carbonate and the like may be used.

Usually, the culture is carried out under aerobic conditions used in shaking culture or aeration agitation culture, at 37° C. Adjustment of the pH of the medium is carried out with an inorganic or organic acid, an solution or the like.

During the culture, antibiotics such as ampicillin or tetraycline may be added to the medium if necessary.

When microorganism tansformed with an expression vector containg an inducible promoter is cultured, an inducer may be added to the medium if necessary. For example, when a microorganism transformed with an expression vector cotaining Lac promoter is cultured, isbpropyl-β-D-thiogalactopyranoside (IPTG) orthe like may be added. When a microorganism transformedwiith an expression vector containing trp promoter is cultured, indoleacetic acid (IAA) or the like may be added.

As a medium for culturing the transformant obtained fron an animal cell as a host, commony used RPMI1640 medium or DMEM medium, or one of these media supplemented with fetal calf serum ect. may be used. Usually, the culture of such a transformant is carried out in the presence 5% at 37° C. for 1 to 30 days. During the culture, antibiotics such as kanamycin or penicillin may be added to the medium if necessary.

After the culture, the choline monooxygenase protein of the invention is extraced by disrupting the cultured microorganisms or cells if the protein is produced in the microorganisms or cells. If the protein of the invention is produced outside of the microorganisms or cells, the culture fluid is used as it is or subjected to centrifugation to remove the miroorgasms or cells, Thereaftcr, the resultant supernatat is subjected to conventional biochemiacal techniques used, for isolating/purifying. These techniques include ammonium sulfate precipitation, gel chromatography, ion exchange chromatography and affinity chromatography, these techniques may be used indepently or in an appropriate combination to thereby isolate add purify the protein of the invention from the above culture.

When the host is a plant, the choline monooxygenase of the invention can be produced by culturing or cultivating the transformed plant. Further, it is also possible to produce the product of a racon catalyzed by the choline monooxygenase, or the interrediates and/or the final product (e.g. betaine) of a series of biosynthesis reactions fllovwing the above rraction.

When the transformant is a plant cell or plant tissue, culture may be performed in a conventional plant culture mediwn, e.g. MS basal medium (Murashige, T. & Skoog F. (1962) Physiol. Plant. 15: 473), LS basal medium (Linsmaier, E. M. & Skoo, F. (1965) Physiol. Plant. 18: 100), or protoplast culture medium (modified LS medium). Conventional solid culture methods my be used, but it is preferable to use liquid culture methods.

A transformed plant cell, tissue or organ is inoculated into the above medium at a rate of 0.1–2.0 g fresh weight/liter. If necessay, NAA, 2.4-D, BA, kinetin or the like is added to the medium appropriately. Then, the transformant is cultured. The pH of the medium at the start of culture is adjusted to 5–7. Usualy, the culture is performed at 20–30° C., preferably at around 25° C., under aeration 0.2–1 vvm and agitation at 50–200 rpm for 1–6 weeks.

When the transformnt is a plant body, it may be cultivated on a field or in a glass house. or may be hydroponically cultured.

In order to recover the protein of the invention from cultred cell or tissues, first the cells are disrupted by cell lysis treatment using an enzyme such as cellulase or pectinase, sonication, grinding or the like. Then, insoluble matters are removed therefrom by filtration, centrifugatiou, etc. to thereby obtain a crude protein solution or a solution containing the primary and/or the secondary metabolite of the plant.

In order to further purify the protein of the invention from the above crude protein solution, conventional protein purification methods may be used. For example, ammonium sulfate salting out, ion exchange chromatography, hydrophobic chromatography, gel filtration chromatography, affinity chromatography or electrophoresis may be used independently or in an appropriate combbination.

In order to recover the protein of the invetnion from plant organs or plant bodies, first, an extact of the useful substance is prepared by disrupting the plant organs or bodies by sonication or grinding. Subsequently, the above-described purification procedures may be followed.

4. Transit Peptides (1) Spceecication of Transit Peptide Sequences

The transit peptide of the invention is a peptide comprising the amino acid sequence shown in SEQ ID NO. 17. The location of this amino acid seqence can be specified by sequence analysis of the cloned choline monooxygenase (CMO) gene. This amino acid sequence is coded by the nucleotide sequce shown in SEQ ID NO: 16.

Once the amino acid sequence has been known, the ttransit peptide of the invention may be produced by chemical synthesis as described below.

(2) Cheiical Synthesis of Transit Peptides

The transit peptide of the invention may be produced by conventional peptide systheis techniques base on the amino acid sequence specified as described above. Either the the liquid synthesis method or the solid synthesis method may be used. Such peptide synthesis may be perforned by any of the kmown methods (see, for example, Bodansz, M. and M. A. Ondetti, Peptide Synthesis, Interscience Publishers, New York (1966); Schroeder and Luebke, The Peptide, Academic-Press, New York (1965); F. M. Finn and K. Hofmann, The Proteins, Vol. 2, H. Nenrath and R. L. Hill (eds.). Academic Press Inc., New York (1976); N. Izumiya et al., Basics aid Experiments in Pcptide Synthesis, Maruzen Co., Tokyo. (1985); H. Yajima, S. Sakakibara et al., Course of Biochemisy Experent Lecture No. 1. The Japanese Biochemical Society (ed.), Tokyo Dojin Co., Tokyo 1977; T.

Kimura, 2nd Series Sakakibara et el., Course of Biochemistry Experiment Lectures No. 2, The Japanese Biochemical Society (ed.), Tokyo Kagaku Dojin Co., Tokyo 1987). Thus, the transit peptide of invention can be obtained by, for example, the azide method, the acid chloride method, the acid anhydide method, the mixed acid anhydride method, the DCC method, the active method, the method using Woodward's reagent K, the carbonylimidazole method, the oxidation-reduction method, tbe DCC/HONB method, or the method using BOP reagent. Usually, the transit peptide may be synthesized with commercial, automated peptide synthesizer.

The transit peptide of the invention can be prepared by ligating a peptide of interest to a peptide fragment of the transit peptide by condensation and then removing the protecting, groups of the C-teminal carboxyl and N-terminal α amino groups of the resulant product at the sane time or in a stepwise manner.

After complction of the reaction, the thus prepared peptide can be recovered by a combination of peptide separaiont/purification techniques such as solvent extration, distillation, partition, recipitation, recrystallization, column chromatography, high perfomance liquid chromatography, gel filtration, ion exchange chromatography and ion exchange chromatography.

The transit peptide of the invention may be obtained in the fornn of a metal salt; a salt made of the peptide and a base or basic compound; an inorganic acid addition salt; an organic salt; or the like. In particular, the transit peptide of tbe invention can b obtained as a pharmaceutically acccptable acid addition salt (e.g. a salt made of the peptide and an inorganic or organic acid). Specific examples of acid addition salis include salts made of the peptide and inorganic acids suc has hydrochloric acid, phosphoric acid, hydrobromic acid, sulfuric acid; or salts made of the peptide and organic acids such as acetic acid, formic aid, proponic acid, fumaric acid, maleic acid, succinic acid, tartaric acid, citric acid, malic acid, oxalic acid, benzoic acid, methanesulfonic acid, benzenesulfonic acid. Specific exsmple of basic salts include salts madef the peptide and inorganic bases such as sodium hydroxide, potassium hydroxide, ammonium hydroxide, magnesium hydroxde; or salts made of the peptide and organic bases such as caffeine, piperidine, trimethylamine, pyridine. Specific eamples of mctal salts include sodium salts, potassium salts, calcium salts and magnesium salts.

The salt of the transit peptide of the invention cam be prepared usin an appropriate acid such as hydrochloric acid or an appropriate base such as sodium hydroxide. For example, the peptide maybe treated with such an acid or base in water or a liquid cotaining an inactive, water-miscible orgnic solvent such as methnol, ethanol or dioxane according to a standard protocol to thereby prepare a salt. The treatment temperature may be from 0 to 100° C.; room temperature is preferable.

The biochemical and physicochemical properties of the transit peptide of the invention can be anayzed by mass spectrometic analysis, nuclear magnetic resonance, electrophoresis high pformance liquid chromatography, etc.

5. Constucon of a Complex Cornposed of Gene of Interest and Transit Peptde Gene, and Induction of Substance Accumulation In the present invention, a gene encoding the trasit peptide (i.e. peptide having a function as a signal peptide) of the invention is ligated upstream of a gene of interest. A DNA complex can be obtained by digesting the gene of interest and the transit peptide gene with appropriate restriction enzymes and then ligating these two genes to each other using ligase. The thus ligated DNA is ligatod to a vector predigested with appropriate restriction enzynme to thereby obtain a recombinant vector. The resultant vector is introduced into a host totby obtain a transformant. By culturing or cultivating the resultant transformant, an expression product of the gene of interest or a metabolite generated through the metabolism of the above expression product by the host can be accumulated. Construction of the recombinant vector, selection of the host and trasformation my be performed in the same manner as described above for the choline monooxygenase of the invention.

As the gene of interest a gene encoding a polypeptide or enzyme may be given, but other genes may also be used. When the expression product of inest is an enyzme, the of a reaction catalyzed by the enzyme or the intermediates and/or the final product (primary or secondary melabolite of plants) of a series of biosynthesis reactons following the above reaction myy be accumulated as useful substances. Spcific examples ofsuch useful subsances include a substame that confers environmental stress resistance, e.g. betaine. Further, when tbe gene interest is a control gene (also called "master gene") in in charge of the functional regulation of an entire reaction pathway (such as biosynthesis pathway) in mechamisms for signals from phosphatases or G-protein, the intermediatcs and/or final product of the reaction pathwat located downstream of the signal transduction of the above control gene may also be accumulated as usefil substances. Tese substances may or may not be involved in environmental stres resistance.

When the transformant (in particular, transformed plant) thus obtined is cultured or cultivated under enviromental stress conditons, an expression product of the gene of interest or a plant metabolite from the expression product is accumulated in the plant upon receipt of the environmental stress as a signal. Specific examples of invironmental stresses includc salt stress, dehydration stress, low stress and high temperature stress.

Salt stress is loaded by adding sodium chloride to a specific hydroponic solution to givc a concentaon of 50–600 mM and culturing the transformed plant therein under useful conditions.

Dehydration stress is loaded by withdrawing the entire plant body from the soil or hydroponic solution and exposing it to the air, or by adding polyethylene glycol or the like to the hydroponic solution or medium.

High terperature or low temperature stess is loaded by rising or lowering the temperature of the incubator, green house, etc. in which the transformed plant is cultured or cultivated.

After loaded with stress, the plant is cultured or cultivated in the same manner as described earlier for the culturing of the transformant, to thereby obtain an environmental sss resistant plant The tean "environmental stress resistant" means the state of a plant that does not wither even under conditions which wither non-resistant plants or that is able to grow evcn under conditions which terminate the growth of non-resit plants, when a particular stress (eg. salt stress. dehydration stess) has been load.

In the present invention, it is possible to allow the expression of a choline monooxygenase-transit peptide complex by ligating a DNA encoding a transit peptide (SEQ ID NO: 16) to a DNA encoding choline monooxygenase (SEQ ID NO. 1, 3 or 5) as a gene of interest and incorporating the resultant construct into an expression vector. In, this case, a choline monooxygenase gene with a DNA encoding a transit petide is incorpoeated in the environmental stress resistant plant of the irvention. When this plant is cultivated under an environmental stress as described above, accumulation of choline monooxygenase is in induced. As a result, synthesis of betaine aldehyde from choline is catalyzed and, finally, betaine is accumulated in the plant. Such accmultion of betaine is significnt in a sense that it can confer environmental stress resitance on the plant. For recovering betaine from plants, methods for purifying quatemary ammonium compounds may be employed.

PREFERRED EMBOIDMENTS OF THENVENTION

Hereinbelow, the present invention will be described more specifically with reference to the following Examples. However, the technical scope of the inventionis not limited to these Examples. In the Examples, choline monooxygenase is expressed as "CMO" or "CMO protein" ad choline monooxygenase gene as "cmo" or "cmo gene".

EXAMPLE 1

Preparation of RNA

*Chemopodium album* mature leaves (4 g) immediately after harvest were disrupted in liquid nitrogen with a blander. To the disrupted leaves, 20 ml of a guanidine thiocyanate solution (4.2 M guanidine thiocyannite, 25 mM sodium citrate dihydrate; immediately before. use, 7 $\mu$ of 2-mercaptoethanol and 5 mg of sodium lauroyl sarcosinate are added per milliliter. of the solution) was added and shaken vigorously for 10 min at room temrature. The resultant mixture was centrifuged at 10,000 rpm for 10 into obtain a supematant, to which 1 g of CsCl was added per 2 ml. This supemtant (6–7 ml) was overlayered upon 4 ml of 5.7 M , CsCl solution (5.7 M CsCl, 0.1 M EDTA (pH 7.5)) contained in an polyalomer tube and ultra-centrifuged at 35,000rpmat20° C. for 18 hr.

The resultant precpitae was dissolved completely in 5 ml of Tris-SDS solution (50 mM Tris-HC (pH 9.0), 1% SDS). To this solution, 5 ml of phenol (pH 9.0) was added and sshaken at room temperature for 10 min. Then, the resultant solution was centrifuged at 5,000 rpm at 20° C. for 10 min. To the resultan supemat 5 ml of phenol/chloform was added and shaken at room temperature for 10 min. Then, the restant solution was centrifuged at 5,000 rpm 20° C. for 10 min, To the resltant supenatant, 5 ml of chloroform was added and shaken at room temperature for 10 min. Then, the resultant solution was centrifuged at 5,000 rpm at 20° C. for 10 min. To the resultant supematant, 1/10volume of 3 M NaOAc was added. Then, 2 volumes of EtOH was added thereto and mixed. The mixture was left at −20° C. for 30 min, followed by centrifugation at 10,000 rpm at 40° C. for 10 min. The resultant precipitate was dissolved in 1 ml of $H_2O$ to thereby obtain RNA from *Chenopodium album* mature leaves.

EXAMPLE 2

Acquisition of a Gene Fragment by RT-PCR and Cloning of the Full-Length Gene (1) Acquisition of a Gene Fragment by RT-PCR Agene fragment was obtained using RT-PCR Kit (Stratagene) according to the protocol attacbed to the kit basically. PCR primers were designed based on the amino acid sequence of spinach CMO.

*Chenopodium album* RNA (9.5 $\mu$g) was dissolved in 38 $\mu$l of DEPC-treated $H_2O$. Three microliters of random primer (100 g/$\mu$l) was added thereto, followed by incubation at 65° C. for 5 min. Then, the solution was cooled slowly to room temperature. To this solution, 5 g $\mu$l of 10×1st strand buffer, 1 $\mu$l of RNase Block Ribonuclease Inhibitor(40 U/$\mu$l), 2 $\mu$l of 100 mM dNTPs and 1 $\mu$l of MMLV reverse transcriptase (50 U/$\mu$l) were added and reacted at 37° C. for 1 hr. Ater the reaction, the reaction solution was incubated at 90° C. for 5 min and then placed on ice. Using 5 $\mu$l of the thus obtained 1st strand cDNA solution as a template, the following PCR reaction solution was prepared and incubated at 91° C. for 5 min and at 54° C. for 5 min.

| Composition of the PCR Reaction Solution: | |
|---|---|
| 1st strand cDNA solution | 5 $\mu$l |
| 10x Ex Taq buffer (Takara) | 10 $\mu$l |
| dNTPs mix (2.5 mM each) | 8 $\mu$l |
| Primer 1 (SEQ ID NO: 7) | 100 pmol |
| Primer 2 (SEQ ID NO: 8) | 100 pmol |
| Total volume | 99.5 $\mu$l |

Subsequently, 0.5 $\mu$l of Takara Ex Taq DNA polymerase (5 U/$\mu$l) was added to the reaction solution. Then, a PCR reaction was performed 30 cycles, one cycle consisting of denaturation at 91° C. for 1 min, annealing at 54° C. for 1 min and extension at 72° C. for 2 mim. After the reaction, the reaction solution was subjected to agarose gel electrophoresis. A fragment of approx. 600 bp which was believed to be the product of interest was cut out from the gel, purified, cloned into pT7Blue T-Vector (Novagen) and sequenced to thereby obtain a *Chenopodium album* cmo gene fragment.

(2) Purification of mRNA

Purifcation of mRNA was performed using mRNA Purification Kit (Pharmacia) and according to the protocol attached to the kit. Briefly, 0.9 mg of total RNA. from *Chenopodium album* was dissolved in 1 ml of an elution buffer. The solution was heated at 65° C. for 5 min and then immediately ice-cooled. To this solution, 0.2 ml of a sample buffer was added, and the resultant solution was applied to an oligo (dT)-cellulose spin column pre-equilibrated with a high-salt buffer. After elution, the column was centrifuged at 350×g for 2 min. Subsequently, the column was washed by adding thereto 0.25 ml of a high-salt buffer and centifuging at 350×g for 2 min; these washing operations were performed twice. Then, similar washing operations were performed 3 times using 0.25 ml of a low-salt buffer.

RNA was recovered by repeating the following operations 4 times: addition of 0.25 ml of an elution buffer preheated to 65° C. and centrifugation at 350×g for 2 min. The resultant RNA solution (1 ml) was colum-purified again in the same manner as described above. To 1 ml of the resultant RNA solution, 100 $\mu$l of a sample buffer, 10 $\mu$lof a glycogen solution and 2.5 ml of EtOH were added, and the resultant solution was left at −20° C. for 2 hr. Then, the solution was centrifued at 14,000 rpm at 4° C. for 10 min. The precipitate was dissolved in 20 1 $\mu$l of $H_2O$, followed by the determination of absorbance.

Thus, 21 $\mu$g of mRNA was obtained.

(3) Synthesis of cDNA (3-1) Synthesis of 1st Strand cDNA

Water was added to 1 $\mu$g of *Chenopodium album* mRNA and 1 $\mu$l of cDNA synthesis primer (10 $\mu$M) to give a 5 $\mu$l solution, which was heated at 70° C. for 2 min and immediately cooled on ice for 2 min. To this solution, 2 $\mu$l of 5×1st strand buffer, 1 $\mu$l of dNTPs mix (10 mM), 1 $\mu$l of MMLV reverse transcriptase (100 U/μl) and 1 μl of H₂O were added After heating at 42° C. for 1 hr. the solution was immediately cooled on ice.

(3-2) Synthesis of 2nd Strand cDNA

Ten microliters of the 1st strand reaction solution, 16 μl of 5× 2nd strand buffer, 1.6 μl of dNTPs mix (10 mM), 4 μl of 20×2nd strand enzyme cocktail and 48.4 μl of H₂O were. mixed gently on ice, and the mixture was incubated at 16° C. for 45 min. Then, the reaction was terminated by adding the 4 μl of a mixtxe of EDTA and glycogen. To the reaction solution, 100 μl of a mixture of phenol:chloroform:isoamyl alcohol (25:24:1) was added and vortexed. Then, the solution was centrifuged at 14,000 rpm for 10 min. To the resultant supemmnt 100 μl of a of phenol:isoamyl alcohol (24:1) was added and vortexed, followed by centrifigation in the same manner as described above. To the resultant supernatant, ½ volume of 4 M monium acetate and 25 volumes of EtOH were added, followed by centrifugation at 14,000 rpm for 20 min. The precipitate was rinsed with 80% EtOR, vacuum-dried and then dissolved in 10 μl of H₂O. Two microliters of this solution was subjected to 0.8% agarose gel eletrophoresis for confirmation. Thus, double stranded (ds) cDNA was obtained.

To 5 μl of the ds RNA, 2μl of Marathon cDNA adaptor (10 μl M), 2 μl of 5×DNA lignation buffer and 1 μl of T4 DNA ligase (1 U/μl) were added and incubated at 16° C. overnight. After deactivation of the ligase by heaing at 70° C. for 5 min, 1 μl of the reaction solution was diluted with 250 μl of Tricine-EDTA buffer. The diluted soluti was heated at 94° C. for 2 min and then cooled on ice for 2 min, to thereby obtain an adaptor-ligated cDNA for use in RACE PCR.

(4) 5' and 3' RACE-PCR

On 5 μl of the adaptor-ligated cDNA as a template, a PCR was peformed using Advatage Klen Taq polymerase (Clontech). Then, 5 μl of the on solution was subjectd to 0.8% agarosc gelectrophoresis for confirmation of the amplified product.

For 5' RACE-PCR, primer 3 (SEQ ID NO: 9) was used. For 3' RACE-PCR, primer 4 (SEQ ID NO: 10) was used.

| Composition of the PCR Reaction Solution: | |
|---|---|
| H₂O | 36 μl |
| 10 mM dNTPs mix | 1 μl |
| 50× Klen Taq polymerase mix | 1 μl |
| 10× Klen Taq buffer (Clontech) | 5 μl |
| Adaptor-ligated cDNA | 5 μl |
| 10 μM AP1 primer (Clontech) | 1 μl |
| 10 μM Primer (primer 3 or primer 4) | |
| Total: | 50 μl |

PCR conditions were as follows: first denaturation at 94° C. for 1 min, then 5 cycles of reaction at 94° C. for 30 sec and at 72° C. for 4 min; then 5 cycle of reaction at 94° C. for 30 sec and at 70° C. for 4min; and finally 25cycles of reaction at 94° C. for 30sec and at 68° C. for 4 min.

An approx. 1.3 kbp band which was believed to be the 5' RACE product and an approx. 12 kbp band which was believed to be the 3' RACE product were conifmed. Each of these bands was cut out from the agarose gel, purified and cloned into pT7Blue T-vector. The nuclcotdc sequence of each clone was determined by the dye-terminator method and analyzed. As a result, it was found that three cmo genes of type A (SEQ ID NO: 1),typ B (SEQ ID NO: 3)and type C (SEQ ID NO. 5) exist.

The amino acid sequences encoded by type A, type B and type C genes are shown in SEQ ID NOS: 2, 4 and 6, respectively.

(5) Acquisition of the Full-Length Type C cmo Gene

Among the three cmo gmm genes, the type C gene was selected for future analysis. Then, the inventors isolated the full-Iength nucleotide sequence of type C cmo gene.

Briey, a PCR reaction was performed using a SmaI site-added primer (primer 5)(SEQ ID NO: 11), an XbaI site-added primer (primer 6)(SEQ ID NO: 12) and KOD DNA polymerase (Toyobo), and the amplified product was ligated to pT7Blue T-vector (Novagen). The PCR was performed 30 cycles, one cycle consisting of denaturation at 94° C. for 1 min, anmealing at 60° C. for 1 min and extension at 72° C. for 2 min.

| Composition of the PCR Reaction Solution: | |
|---|---|
| Primer concentration 20 pmol | |
| 2 mM dNTPs | 5 μl |
| Adaptor-ligated cDNA | 10 μl |
| 25 mM MgCl₂ | 2 μl |
| KOD DNA polymerase (2.5 U/μl) (Toyobo) | 1 μl |
| 10× PCR buffer (Toyobo) | 5 μl |
| Total: | 50 μl |

The nucleotide sequence of the amplified product was determined by the dye-terminator method to thereby confirm that the product was type C gene. This was designated "pT7cmo".

(6) Preparation of Antibodies to CMO Protein

In order to analyze the expression of CMO protein, antibodies to CMO protein were prepared using Xpress System (Initrogen):

Briefly, 5' priner (primer 7)(SEQ ID NO: 13) to which BamHI sit added and 3' primer (primer 8)(SEQ ID NO: 14) to which a KpnI site was added were pepared for amplifying the code region of the protein excluding the transit peptide. Using these primers, a PCR was performed to thereby amplify an approx. 1.2 kbp fragment. The PCR was performed 30 cycles, one cycle consisting of denaturation at 94° C. for 1 ml, annealing at 60° C. for 1 min and extension at 72° C. for 2min.

| Composition of the PCR Reaction Solution: | |
|---|---|
| H₂O | 78 μl |
| 4 mM dNTPs mix | 8 μl |
| Ex Taq (5 U/μl) (Takara) | 0.5 μl |
| 10× Ex Taq buffer (Takara) | 10 μl |
| pT7cmo (1 ng/μl) | 1 μl |
| 10 μM Primer (primer 7 + primer 8) | |
| Total: | 100 μl |

The amplified product was ligated to pT7Blue T-vector (Novagen) and designated "pT7cmoA". pT7cmoA and pTrcHis were digested with resricton enzymes BamHI and KpnI, and separately subjected to 0.8% agrose gel electrophoresis. Using Gene Clean Spin Kit (BIO 101), a cmo gene fragment of approx. 1.2 kbp and a vector fragment of approx. 4.4 kb were recovered from the gel according to the manual attached to the kit. Afer purificion, these two fragments were ligated to each other in a reaction system of 50 μl, using DNA Ligation Kit (Takara) utiliing T4 DNA ligase, and the thus ligated DNA is refcrrecd to as pTHC. The ligood DNA was introduced into *E. coli* (JM 109; Takara) to thereby prepare a fusion protein The thus prepare pTHC was purifed by the niniprep method and intrduced into *E. coi* TOP10; Invitrogen)

according to the manual attached to TOP10. The pTHC-introduced *E. coli* was cultured accordig to the manual ached to Xpress System (Ivitrogen). From 400 ml of the resultant culture liquid, histidine-labelled CMO protein was prepared and applied to a Probond resin colum (Invitogn). Thus, approx. 10 mg of the protein was iimmobilized in the column. From this column, 350 mM imidazole fraction was reovered, followed by removal of imidazole with PB10 (Pharmacia). The resultant solution was applied to a Pro-bond resin column (Ivitrigen) again to immobilize the protein. Two hundred units of enterokinase was mixed with approx. 4.5 mg of the i obimmzo fusion protein and shaken at room temperaure fbr 10 hr. In 4 ml of the eluate from this column, the presence of a 43 kDa protein (equivalent to 1.6 mg of CMO mature protein) was confin by SDS-PAGE.

After purification, this CMO protein was administered to rabbits as antigen to prepare anti-sera, which were used as antibodies.

EXAMPLE 3

ConrtruCtion of Expression Vectors

For the purpose of expressing *Chenopodium album* cmo gene in tobacco, two types of expession vectors were prepared. One was pBIcmo comprising the DNA shown in SEQ ID NO: 16encoding the tansit peptide (SEQ ID NO: 17), and the other was pBIcmoS not comprising the DNA encoding the transit peptide.

First a SmaI site-added primer (primer 9) (SEQ ID NO: 15) was prepared in order to amplify a cmo gene sequence without the region encoding the transit peptide.

Using this priiner as 5' primer and pimer 6 (SEQ ID NO: 12) as 3' primer, a PCR reaction was performed to amplify a gene fragment without the region encoding the transit peptide. The amplfifed fragment was ligated to pT7BDue T-vector (Novagen), which was designated pT7cmoS. The PCR was performed 30 cycles, one cycle consisting of denaturation at 94° C. for 1 min, amnealing at 60° C. for miand exteson at 7290 for 2in.

| Composition of the PCR Reaction Solution: | |
|---|---|
| H₂O | 78 μl |
| 4 mM dNTPs mix | 8 μl |
| Ex Taq (5 U/μl) (Takara) | 0.5 μl |
| 10x Ex Taq buffer (Takara) | 10 μl |
| pT7cmo (1 ng/μl) | 1 μl |
| 10 μM Primer (primer 9 + primer 6) | |
| Total: | 100 μl | pT7cmo and pT7cmoS were separately digested with restriction enzymes SacI and SmaI, and subjected to agarose gel electrophoresis. Then, an approx. 1.2 kps band and an approx. 1.4 kbp band were cut out from the gel and purified. pBI121 (purchased from Clontech) was digested with restriction enymes SacI and SamI, and then an approx. 11 kbp band was cut out and purified in the same mamner. This band was ligated to each of the above-mentioned fragments to thereby prepare pBIcmo and pBIcmoS.

EXAMPLE 4

Gene Trnsfer into Tobacco (1) Transformation of *Agrobacterium tumefaciens*

*Agrobacterium tumefaciens* LBA4404 (purchased from Clontech) was cultured in L medium containing 250 μg/ml streptomycin an 50 μg/ml rifampicin at 28° C. A cell suspension was prepared from the culture accoording to the method of Nagel et al. (Microbiol. Lett., 67:325, 1990). Then, pBIcmo and pBIcmoS were separately introduced into the above-mentioned strain.

(2) Transfer of the Polynucleotide Encoding CMO into Tobacco Cells

Using the transformed *Agrombacterium tumefaciens* obtained in (1) above, transfonmation of *Nicotiana tabacum* cv. SR1 was peformed according to the method of Horschet, et al. (Science, 277: 1229–1231, 1985).

In each of the following Examples, those lines which were homozygous with to the transgene were selected from R1 gmneraton of the cmo gene-transferred tobacco that had been obtained through redifferntiation, and used in exparmients. In the cmo geen transferred tobaco as obtained above, CMO protein is constantly expressed since the poly-nudeotide of the invention encoding CMO is under the control of CaMV35S promoter which is a high expression pnomoter.

EXAMPLE 5

Metod of Tobaco Cultivation

Tobacco seeds were sterilized by shaking them in 40 ml of 10% aqueous solution of sodium bypochloxite (Nacalai Tesque) supplemented with 10 μl of Triton X-100 for 10 min and then washed with 500 ml of sterilized water in parts. The sterilized tobacco seeds were grown in ½ MS mnedium (sucrose cwncenion: 1.5%), which is a medium containing one half (½) of each of the components of Murashige and Skoog (MS) medium (Murshige et al., Physiol. Plant 15:473–497, 1962), at 25° C. under conditions of 16 hr light/8 hr dark for 2 weeks. Thererfter, the resultant seedlings were transplanted to square-shaped pots containing ½ MS medium and subjected to various experiments.

(1) Westem Blot Analysis

The expression of CMO protein was examined at the protein level using the above-described cmo gene-transfered tobacco and a wild-type, non-recombinant tobacco SR1.

Briefly, completely unfolded upper leaves (0.2 g) were taken from cmo gene-transferred tobacco (pBIcmo 4-2 lines and pBIcmaS 53-1 line) and non-recombinant *Nicotiana tabacum* cv. SR1. The sample was disrupted in liquid nitrogen, suspended in 0.4 ml of an extraction buffer (1% SDS, 0.1 M NaHCO₃, 5% 2-mercaptoethanol) and boiled for 5 min. Then, the sample was centrifuged atfl 15,000 rpm for 5 min at room tempeture to obtain the supernatant as a protein extract. This protein extract was separated by SDS-PAGE and transferred onto a nylon membrae (Imobilon; Millipore). This membrane was incubated with the above-described antibody to CMO (5000-fold dilution of the anti-serum) and washed. The membrane was further incu-bated with a secondary body of 3000-fold dilution [affinty-purified goat anti-rabbit IgG (H+L) line phosphatase conju-gate; BioRad] and washed, followed by detection of CMO with a coloring solution (Konica Immunostain HRP-1000; Konica)).

The results of the Western blotting are shown in FIG. 1. The existence of an immune responsive protein of 43 kDa corresponding to CMO was confirmed. In pBIcmo-transferred tobacco, it was shown that accumulation of CMO protein fom which the ttransit peptide had been removed was increased by several times when 150 mM NaCl stress was loaded for 1 day. In pBIcmoS-transferred tobacco, no induction of protin accumnlation was observed when 150 mM NaCl stress was loaded. From these results, it was indicated that a polypeptide sequence corresponding to the *Chenopodium album* CMO transit peptide promotes protein accumulation in response to salt stress.

(2) Determination of Betaine Accumulation in Transformed Plants

Betaine contents in plant leaves were calculated by measuring NMR spectra of quatemary ammonium compounds (Wall, J. et al., Analyt. Chem. 32:870–874, 1960). One gram each of leaves from the wild-type plant and the transformed plant was powdered in liquid nitrogen using a ceramic motor. The resultant powder was suspended in 4 ml of 1.0 M $H_2SO_4$, which was then shaken at 25° C. for 24 hr. After removal of insoluble matters, the susion was centfigured at 1000×g for 10 min to recover a supernatant. To 1 ml of this 0.4 ml of $KI-I_2$ solution was added and shaken at 4° C. for 80 min. The sultant solution was centrifuged at 13,000×g to they recover periodite-addition products of betaine, choline or the like. These products were dissolved in 0.6 nl of D20 (EURISO-TOP) contining t-butyl : alcohol (Nalai Tesque) as an internal standard, followed by measurement of 1H-NMR spectra.

As a result, two major peaks of betaine choline were observed. The integrated value for the betaine peak was used for the quantitative detrmination of betaine concentration.

Tobacco plants grown for 2 weeks after sowig w transplanted to square-sahaped pots contcontaining ½ MS modium supplemented with 20 mM chohmne (Naclai Tisque) and 100 mM NaCl. After 2-week cultivation, samples were collected and used for the quantitative detemination of betaine.

Figure 2:
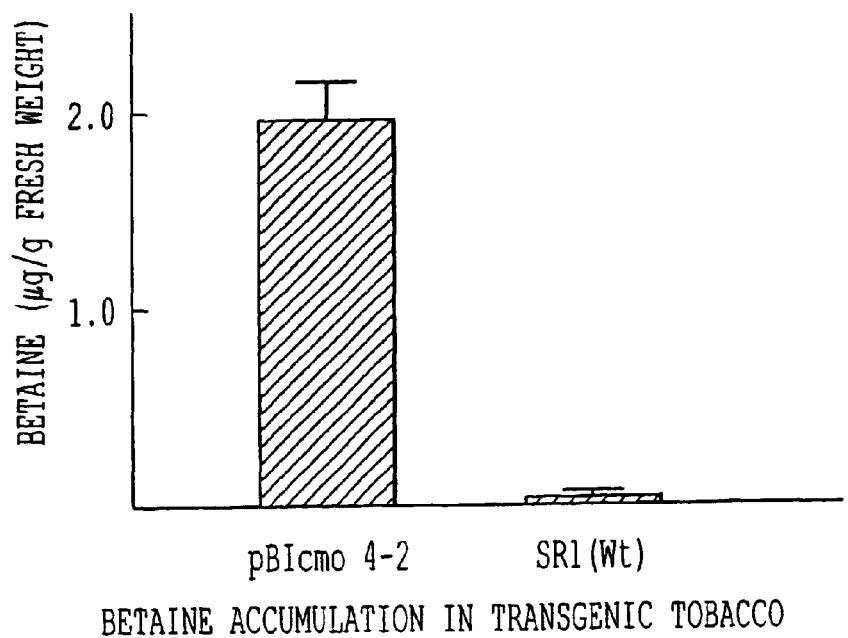
FIG. 2 is a graph showin betaine accumulation in a transgenic tobacco.

As a result, while only choline was observed in the wild-type plants, both betaine and choline were observed in the transformed plants. As shown in FIG. 2, the betaine content of pBIcmo4-2 plant was 2.0 µg/g fresh weight. These results indited that transgenic plants expressing the CMO mature protein have ability to e betaine.

All publications, patents and patent applications cited herein are incorporated by reference in their entirety.

According to the present invention, choline monooxygenase and the gene thereof are provided. The gene is applicable to the breeding of those plants which arm highly tolaant to dry or saline soil. Also, the creation of such plants using the above gene will be helpful to restore plant cultivation in wasteland resulted from dry or saline soil, or to iies the yields of crops in areas of dry soil or saline soil.

---

What is claimed is:

1. An isolated-choline monooxygenase gene encoding a protein comprising the amino acid sequence shown in SEQ ID NO:2, 4 or 6.

2. An isolated gene comprising the following DNA (c) or (d):
  (c) the nucleotide sequence shown in SEQ ID NO: 1, 3 or 5;
  (d) a nucleotide sequence which has 97% homology with the nucleotide sequence. shown in SEQ ID NO: 1, 3or 5, and which encodes a protein having choline monooxygenase activity.

3. A recombinant vector comprising the isolated gene according to claim 1.

4. A transformant comprising the recombinant vector according to claim 3.

5. A method for producing a choline monooxygenase, comprising culturing the transformant according to claim 4 and recovering the choline monooxygenase from the resultant culture.

6. An isolated gene encoding a peptide comprising the amino acid sequence shown in SEQ ID NO:17.

7. An isolated gene comprising the following DNA (g) or (h):
  (g) the nucleotide sequence shown in SEQ ID NO: 16;
  (h) a nucleotide sequence which has 97% homology with the nucleotide sequence shown in SEQ ID NO:16 and which encodes a protein having signal peptide activity.

8. A recombinant vector comprising the isolated gene according to claim 6 or 7 and a gene of interest.

9. The recombinant vector according to claim 8, wherein the isolated gene of interest leads to production of a polypeptide or production of a plant metabolite.

10. The recombinant vector according to claim 8, wherein the polypeptide or the plant metabolite confers stifrs resistance to high salt conditions, drought conditions or both in a tobacco plant.

11. The recombinant vector according to claim 8, wherein the gene of interest is *Chenopodium album* choline monooxygenase gene.

12. A transformant comprising the recombinant vector according to claim 8.

13. The transformant according to claim 12, which is a plant body, plant organ, plant tissue or cultured plant cell.

14. A tobacco plant which is obtained by culturing or cultivating a transformed plant comprising the recombinant vector according to claim 10 under an environmental stress of high salt conditions, drouht conditions or both.

15. The plant according to claim 14, wherein the environmental stress is high salt stress.

16. A recombinant vector comprising the isolated gene according to claim 2.

17. A transformant comprising the recombinant vector according to claim 16.

18. A method for producing a choline monooxygenase, comprising culturing the transfornant according to claim 17 and recovering the choline monooxygenase from the resultant culture.

19. A recombinant vector comprising the isolated gene according to claim 7 and a gene of interest.

20. The recombinant vetor according to claim 19, wherein the gen eof interest leads to production of a polypeptide or production of a plant metabolite.

21. The recombinant vector according to claim 19, wherein the polypeptide or the plant metabolite resistance to high salt conditions, drought conditions or both in a tobacco plant.

22. The recombinant vector according to claim 19, wherein the gene of interest is *Chenopodium album* choline monooxygenase gene.

23. A transformant comprising the recombinant vector according to claim 19.

24. A transformant comprising the recombinant vector according to claim 20.

25. A transformant comprising the recombinant vector according to claim 21.

26. A transformant comprising the recombinant vector according to claim 22.

27. The transformant according to claim 23, which is a plant body, plant organ, plant tissue or cultured plant cell.

28. The transformant according to claim 24, which is a plant body, plant organ, plant tissue or cultured plant cell.

29. The transformant accord ing to claim 25, which is a plant body, plant organ, plant tissue or cultured plant cell.

30. The transformant according to claim 26, which is a plant body, plant organ, plant tissue or cultured plant cell.

31. The trarisformnant according to claim 27, which is a plant body, plant organ, plant tissue or cultured plant cell.

32. A tobacco plant which is obtained by culturing or cultivating a transformed plant comprising the recombinat vector according to claim 11 under an environmental stress of high salt conditions, drought conditions or both.

33. The plant according to claim 32, wherein the environmental stress is high salt stress.

34. The isolated gene according to claim 2, which is (c).

35. The isolatdgn codn to claim 2, which is (d).

36. The isolated gene according to claim 7, which is (g).

37. The isolated gene according to claim 7, which is (h).

38. A tobacco plant which is obtained by culturing or cultivating a transformed plant comprising the recombinant vector according to claim 11 under an environmental stress of high salt conditions, drouht conditions or both.

39. The plant according to claim 38, wherein the environmental stress is high salt stress.

\* \* \* \* \*